United States Patent
Peppas et al.

(10) Patent No.: US 11,000,602 B2
(45) Date of Patent: May 11, 2021

(54) DELIVERY OF SMALL INTERFERING RNA AND MICRO RNA THROUGH NANOGELS CONTAINING HYDROPHOBIC PSEUDO-PEPTIDES

(71) Applicant: Board of Regents, The University of Texas System, Austin, TX (US)

(72) Inventors: Nicholas Peppas, Austin, TX (US); William Liechty, Midland, MI (US)

(73) Assignee: Board of Regents, The University of Texas System, Austin, TX (US)

( * ) Notice: Subject to any disclaimer, the term of this patent is extended or adjusted under 35 U.S.C. 154(b) by 1042 days.

(21) Appl. No.: 15/587,717

(22) Filed: May 5, 2017

(65) Prior Publication Data
US 2017/0312372 A1    Nov. 2, 2017

Related U.S. Application Data

(63) Continuation of application No. PCT/US2015/059220, filed on Nov. 5, 2015.

(60) Provisional application No. 62/076,124, filed on Nov. 6, 2014.

(51) Int. Cl.
| | |
|---|---|
| *A61K 31/713* | (2006.01) |
| *A61K 47/58* | (2017.01) |
| *A61K 47/69* | (2017.01) |
| *A61K 9/06* | (2006.01) |
| *C08F 222/38* | (2006.01) |
| *A61K 31/7088* | (2006.01) |
| *A61K 9/51* | (2006.01) |
| *C08J 3/24* | (2006.01) |
| *C12N 15/113* | (2010.01) |

(52) U.S. Cl.
CPC ............ *A61K 47/6903* (2017.08); *A61K 9/06* (2013.01); *A61K 9/5138* (2013.01); *A61K 9/5146* (2013.01); *A61K 31/7088* (2013.01); *A61K 31/713* (2013.01); *A61K 47/58* (2017.08); *C08F 222/38* (2013.01); *C08J 3/24* (2013.01); *C12N 15/113* (2013.01); *C08J 2335/00* (2013.01); *C12N 2310/14* (2013.01); *C12N 2320/32* (2013.01)

(58) Field of Classification Search
CPC ........ A61K 47/693; A61K 47/58; A61K 9/06; A61K 9/5146; A61K 9/5138; A61K 31/7088; A61K 31/713; C08F 222/38; C08J 3/24; C08J 2335/00; C12N 12/113; C12N 2310/14; C12N 2320/32
See application file for complete search history.

(56) References Cited

U.S. PATENT DOCUMENTS

| | | | |
|---|---|---|---|
| 4,163,092 | A | 7/1979 | Steckler |
| 4,668,506 | A * | 5/1987 | Bawa |
| 5,415,864 | A | 5/1995 | Kopecek et al. |
| 2004/0127648 | A1 * | 7/2004 | Guerrier |
| 2011/0200675 | A1 * | 8/2011 | Thayumanavan |
| 2011/0318267 | A1 | 12/2011 | Auguste et al. |
| 2013/0072576 | A1 * | 3/2013 | Forcada Garcia |

FOREIGN PATENT DOCUMENTS

WO    2014059430    4/2014

OTHER PUBLICATIONS

Yoshida (European Polymer Journal, vol. 25, Issue 12, pp. 1197-1202, Published 1989) (Year: 1989).*
Ozturk, N et al. "Reversible adsorption of lipase on novel hydrophobic nanospheres." Separation and Purification Technology. 2007, vol. 58, No. 1, abstract, pp. 83-90.

* cited by examiner

*Primary Examiner* — Alma Pipic
(74) *Attorney, Agent, or Firm* — Robert R. Riddle; Hallie H. Wimberly; Reed Smith LLP

(57) ABSTRACT

Nanoscale, pH-responsive polycationic networks useful for the delivery of anionic biologic therapeutics and associated methods.

Figure 1:
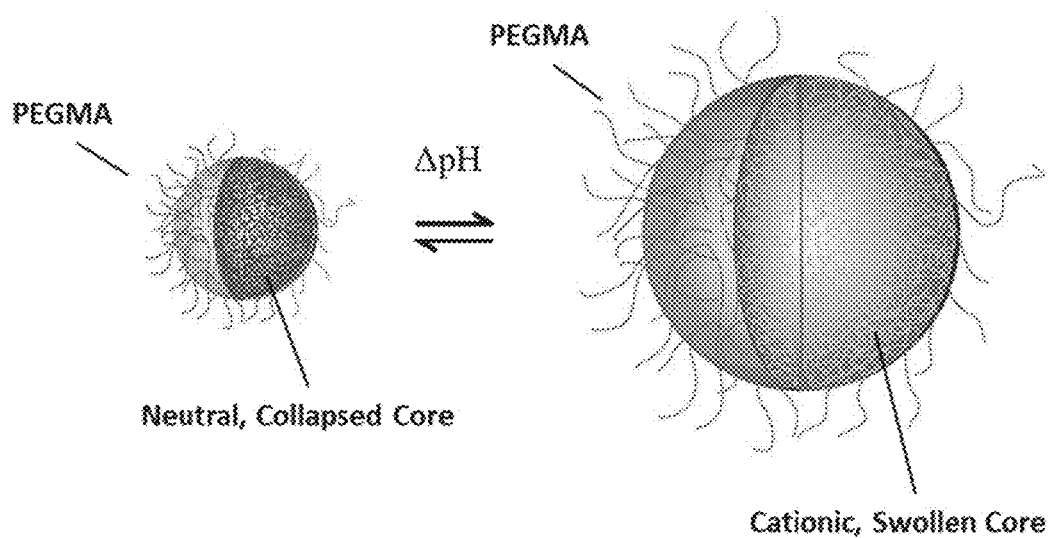

11 Claims, 17 Drawing Sheets
(9 of 17 Drawing Sheet(s) Filed in Color)
Specification includes a Sequence Listing.

L-Phenylalanine methyl ester + Methacryloyl chloride

DCM 4°C, 2 eq. triethylamine

N-methacryloyl – (L) – phenylalanine methyl ester (MAPA)

ppm

SEQUENCE LISTING

<160> NUMBER OF SEQ ID NOS: 1

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

```
<400> SEQUENCE: 1
uaaggcuaug aagagauacu u                                    21
```

DELIVERY OF SMALL INTERFERING RNA AND MICRO RNA THROUGH NANOGELS CONTAINING HYDROPHOBIC PSEUDO-PEPTIDES

CROSS-REFERENCE TO RELATED APPLICATION

This application is continuation of International Application No. PCT/US15/59220, filed Nov. 5, 2015, which was published as International Publication No. WO16/073706, which claims the benefit of U.S. Provisional Application No. 62/076,124, filed on Nov. 6, 2014, the entirety of which is incorporated by reference.

STATEMENT OF GOVERNMENT INTEREST

This invention was made with government support under Grant No. CBET1033746 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Jun. 7, 2017, is named 14-21021-US_SL.txt and is 652 bytes in size.

BACKGROUND

Polymers have played an integral role in the advancement of drug delivery technology, providing controlled release of therapeutic agents in constant doses over long periods, cyclic dosage, and enabling tunable release of both hydrophilic and hydrophobic drugs. From early beginnings using off-the-shelf materials, the field has grown tremendously, driven in part by the innovations of chemical engineers. Modern advances in drug delivery are now predicated upon the rational design of polymers tailored for specific cargo and engineered to exert distinct biological functions. In particular, hydrogels have been instrumental in the development of polymeric systems for controlled release of therapeutic agents. These materials are attractive for transmucosal and intracellular drug delivery because of their facile synthesis, inherent biocompatibility, tunable physicochemical properties, and capacity to respond to various physiological stimuli.

The landmark discovery of RNA interference (RNAi) in 1998 has sparked a massive research effort in all fields of biological science and redefined our understanding of gene regulation mechanisms. Theoretically, RNAi mediated by small interfering RNA (siRNA) could be used as a powerful and versatile treatment modality to treat nearly any disease resulting from aberrant gene expression. Owing to its remarkable potency and low therapeutic dosage, siRNA holds extraordinary promise as a new biological therapeutic. However, efficient delivery has been implicated as the major hurdle to its widespread clinical application. Although much effort has been directed toward synthetic polymer carriers for siRNA, there remains a paucity of data on the development of oral delivery systems. Nearly all delivery systems undergoing clinical trials (no RNAi therapeutic has achieved FDA approval) rely on naked siRNA, conjugated polymers, or lipid carriers for topical and intravenous administration and do not posses attributes that render them useful delivery vectors for GI targets. It is desirable to develop a novel hydrogel platform for delivery of agents, such as agents for RNA interference, and capable of transporting therapeutic cargoes to their subcellular site of action.

SUMMARY

The present disclosure generally relates to compositions useful in the delivery of anionic therapeutic agents. More particularly, in some embodiments, the present disclosure relates to nanoscale, pH-responsive polycationic networks useful for the delivery of anionic biologic therapeutics and associated methods. The present disclosure provides, according to certain embodiments pH-responsive polycationic networks comprising siRNA in the polymer network. Such siRNA-containing networks may be useful for delivery of siRNA.

In this disclosure, a robust synthesis approach to expand the range of therapeutics currently delivered via hydrogel technology is outlined. Through judicious materials selection and careful design of copolymer composition and molecular architecture, systems capable of responding to distinct physiological cues, with tunable physicochemical properties that are optimized to load, protect, and deliver valuable macromolecular payloads to their intended site of action may be engineered.

Embodiments of this disclosure are generally directed to compositions comprising a cationic monomer, a methacrylamide-derivatized hydrophobic amino acid, and a crosslinker. In certain embodiments, the composition comprises a hydrogel comprising a plurality of crosslinked copolymers, wherein a cationic monomer and a methacrylamide-derivatized hydrophobic amino acid are co-polymerized and crosslinked to form the hydrogel. In any of these embodiments, as applicable, the cationic monomer may be 2-(diethylamino) ethyl methacrylate (DEAEMA), the methacrylamide-derivatized hydrophobic amino acid may be N-methacryloyl L-phenylalanine methyl ester (MAPA) and the crosslinker may be poly(ethylene glycol) methyl ether methacrylate (PEGMA). In certain aspects, the composition comprises DEAEMA as the cationic monomer, MAPA as the methacrylamide-derivatized hydrophobic amino acid and PEGMA as the crosslinker.

In any of the embodiments of the present disclosure, the compositions may further comprise a plurality of poly(ethylene glycol) polymers, polyoxazoline polymers or both. In certain aspects, the poly(ethylene glycol) polymers and/or polyoxazoline polymers are covalently attached to the hydrogel. In some embodiments, the poly(ethylene glycol) or polyoxazoline polymers or both are at least partially disposed on an exterior surface of the hydrogel.

In some embodiments, the amount of cationic monomer and methacrylamide-derivatized hydrophobic amino acid is present in a ratio of from about 20% to 50%. In other embodiments, the cationic monomer is from 50 to 80 mol %, and the methacrylamide derivatized hydrophobic amino acid is from 20 to 50 mol %. In certain other embodiments, the cationic monomer is from 50 to 80 mol %, the methacrylate-derivatized hydrophobic amino acid is from 20 to 50 mol %, and the crosslinker is from 0.5 to 5 mol %. In certain embodiments, the composition has a cytocompatibility of greater than 80% when the composition is at a concentration of 100 ug/mL.

In any of the foregoing embodiments, the composition may further comprise an anionic therapeutic agent. In one aspect, the anionic therapeutic agent is disposed within the hydrogel. In some embodiments, the compositions may also further comprise a nucleic acid molecule. In certain aspects, the nucleic acid molecule is a siRNA molecule. In some embodiments, the nucleic acid molecule is disposed within the hydrogel.

In certain embodiments, the hydrogel has a positive surface charge at about pH 7.4. In some embodiments, the hydrogel has a collapsed structure at about pH 7.4. The hydrogel may also have a Z-average particle size diameter of from about 20 nm to about 200 nm.

In some embodiments, the compositions may also be in a pharmaceutical formulation.

In another embodiment, a method comprises providing at a pH of less than or equal to about 6.5, a pH responsive polycationic hydrogel, the hydrogel comprising a plurality of crosslinked copolymers, wherein each copolymer comprises a cationic monomer and a methacrylamide-derivatized hydrophobic amino acid and introducing the pH responsive polycationic hydrogel to an environment having a pH of about greater than or equal to about 7. In certain embodiments, the pH responsive polycationic hydrogel further comprises an anionic therapeutic disposed within the hydrogel. In some embodiments, the pH responsive polycationic hydrogel further comprises a nucleic acid molecule disposed within the hydrogel.

In certain embodiments, the environment is a cell, a disease site in a subject's gastrointestinal tract, a gastrointestinal carcinoma, an active site of Crohn's disease in a subject's gastrointestinal tract, an active site of ulcerative colitis in a subject's gastrointestinal tract, or an active site of celiac disease in a subject's gastrointestinal tract.

The features and advantages of the present invention will be readily apparent to those skilled in the art. While numerous changes may be made by those skilled in the art, such changes are within the spirit of the invention.

DRAWINGS

The patent or application file contains at least one drawing executed in color. Copies of this patent or patent application publication with color drawing(s) will be provided by the Office upon request and payment of the necessary fee. Some specific example embodiments of the disclosure may be understood by referring, in part, to the following description and the accompanying drawings.

FIG. 1—Schematic of pH-responsive hydrogels.

Figure 2:
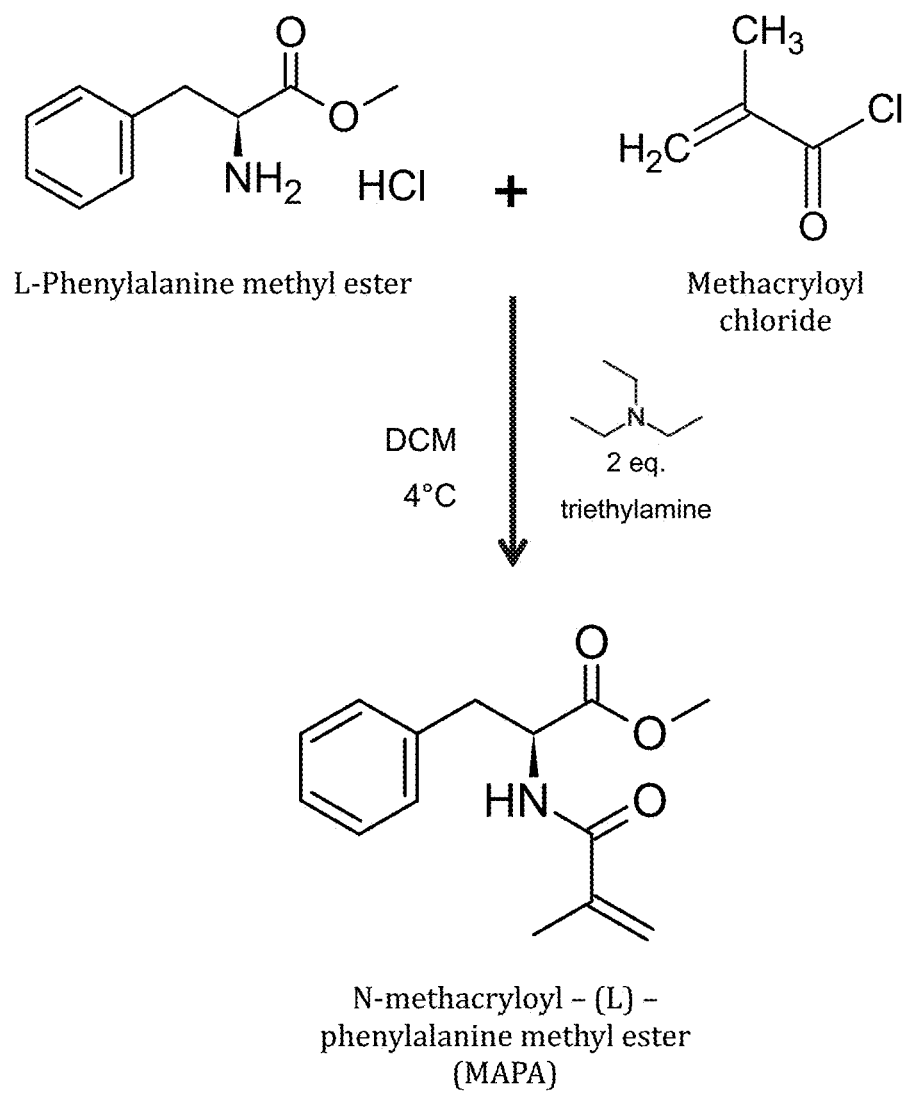

FIG. 2—Reaction scheme for N-methacryloyl L-phenylalanine methyl ester (MAPA) monomer.

Figures 3, 4:
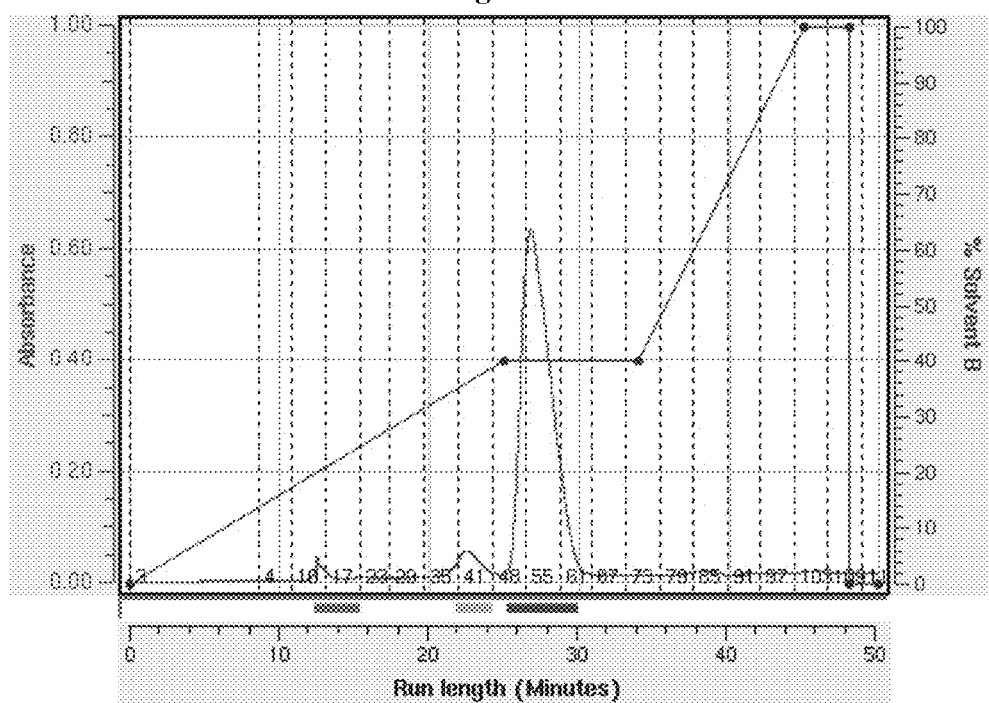

FIG. 3—Purification of MAPA reaction products using flash chromatography. Eluent absorbance at 258 nm is shown in red (left axis) and solvent (Solvent A—hexanes; Solvent B—ethyl acetate) gradient is shown in blue (right axis).

FIGS. 4—$^1$H-NMR Spectrum of purified N-methacryloyl L-phenylalanine methyl ester (MAPA) monomer in $CDCl_3$.

Figure 5:
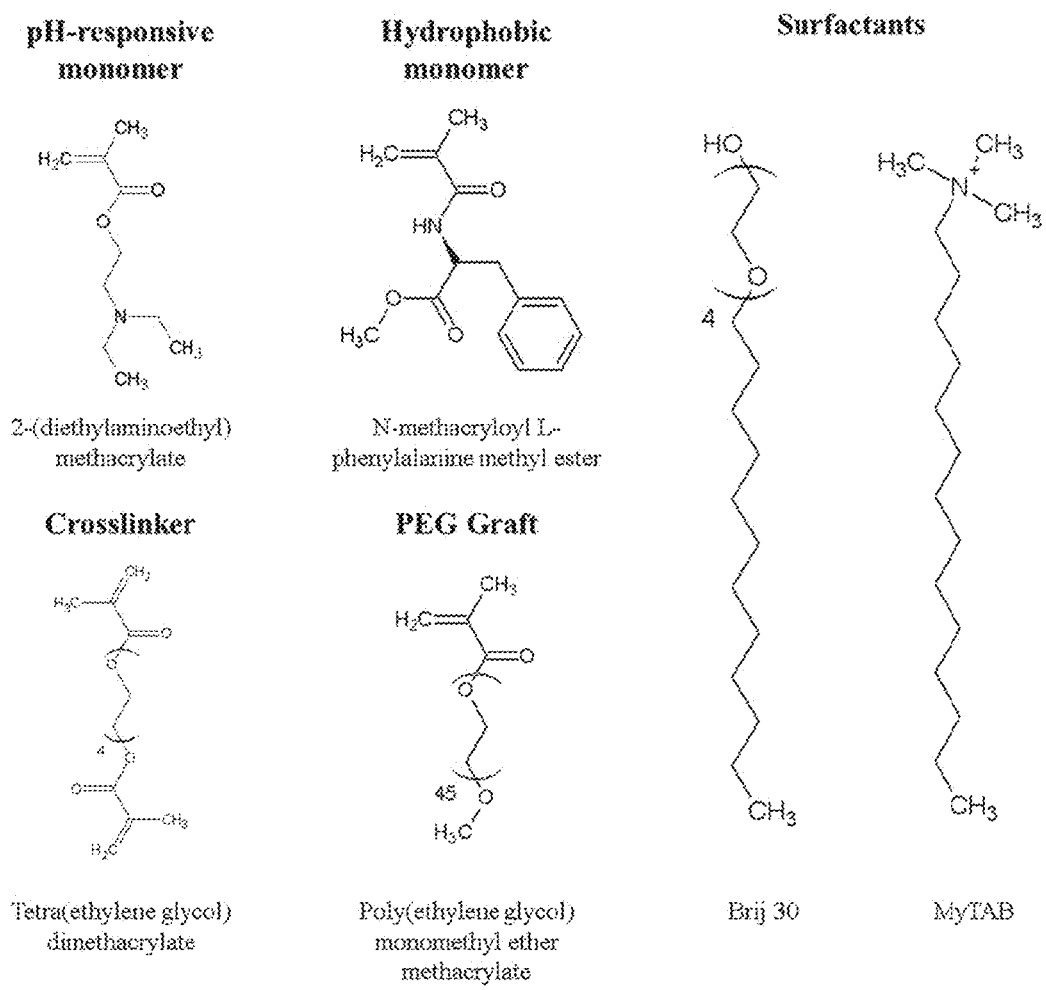

FIG. 5—Monomers and surfactants used in the synthesis of P(DEAEMA-co-MAPA-g-PEGMA) (PDETM30).

Figure 6:
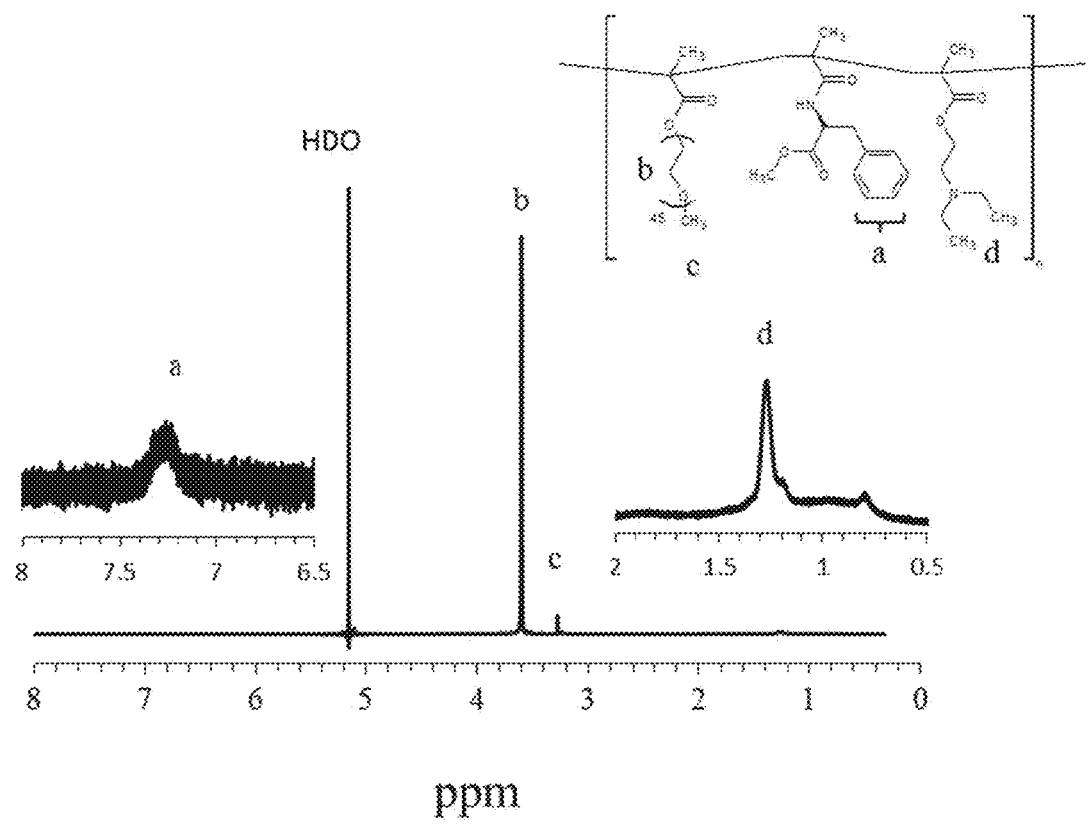

FIGS. 6—$^1$H-NMR spectra of crosslinked P(DEAEMA-co-MAPA-g-PEGMA) (PDETM30) in 0.1 N $DCl/D_2O$.

Figure 7:
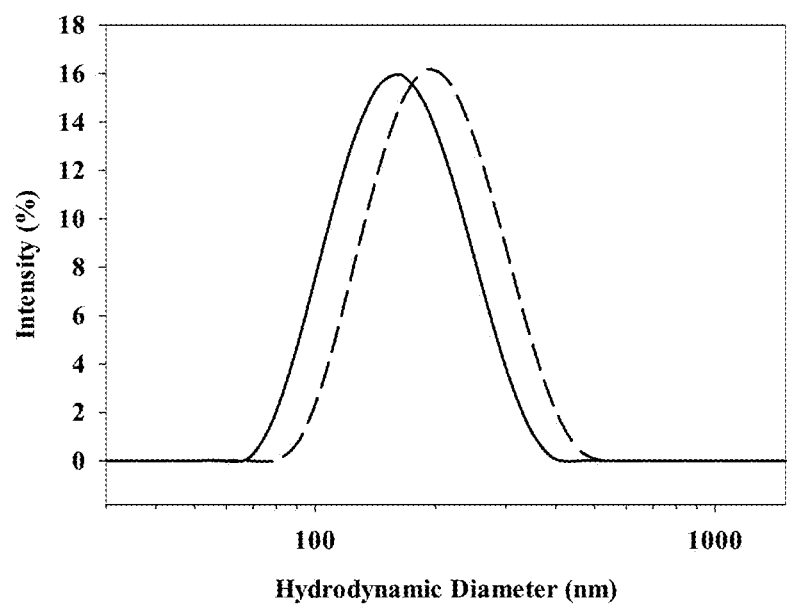

FIG. 7—Representative intensity-weighted particle size distribution for PDETM30 in the collapsed (solid) and swollen (dashed) state. Distribution in the collapsed state is from a measurement at pH 9.0 and distribution in the swollen state is from a measurement at pH 6.0.

Figure 8:
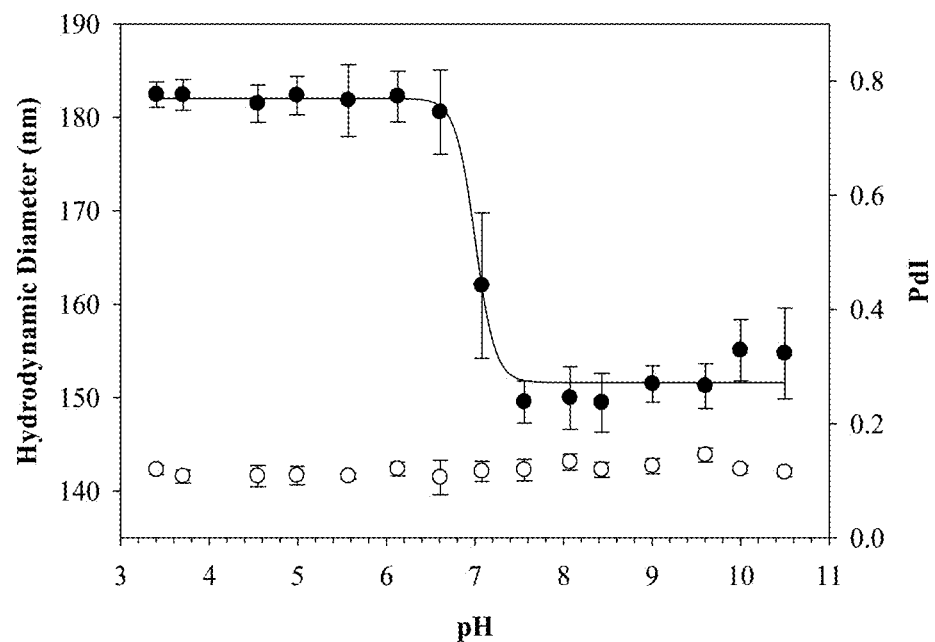

FIG. 8—Z-average diameter (●, left axis) and polydispersity (○, right axis) of P(DEAEMA-co-MAPA-g-PEGMA) networks crosslinked with 2.5 mol % TEGDMA in response to dynamic pH. Data points represent the mean of 3 sequential runs of 12 measurements each and error bars represent the standard deviation. The line represents a hyperbolic tangent best fit.

Figure 9:
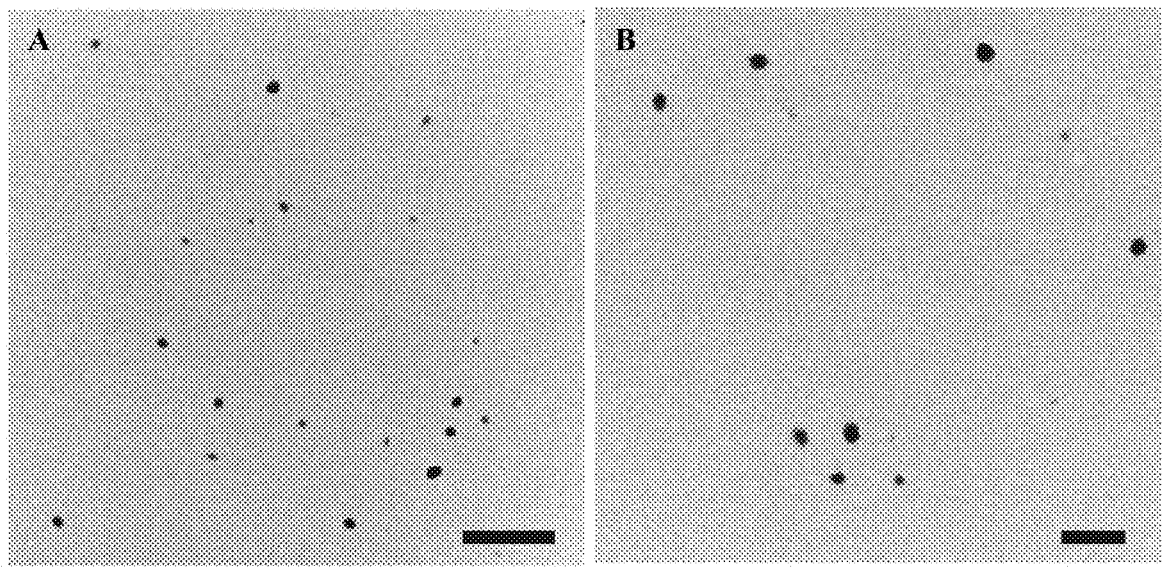

FIG. 9—Representative transmission electron microscopy image of TEGDMA-crosslinked P(DEAEMA-co-MAPA-g-PEGMA). Particles stained with uranyl acetate and images collected at 26,500× (A) and 43,000× (B). Scale bar represents 500 nm (A) or 200 nm (B).

Figure 10:
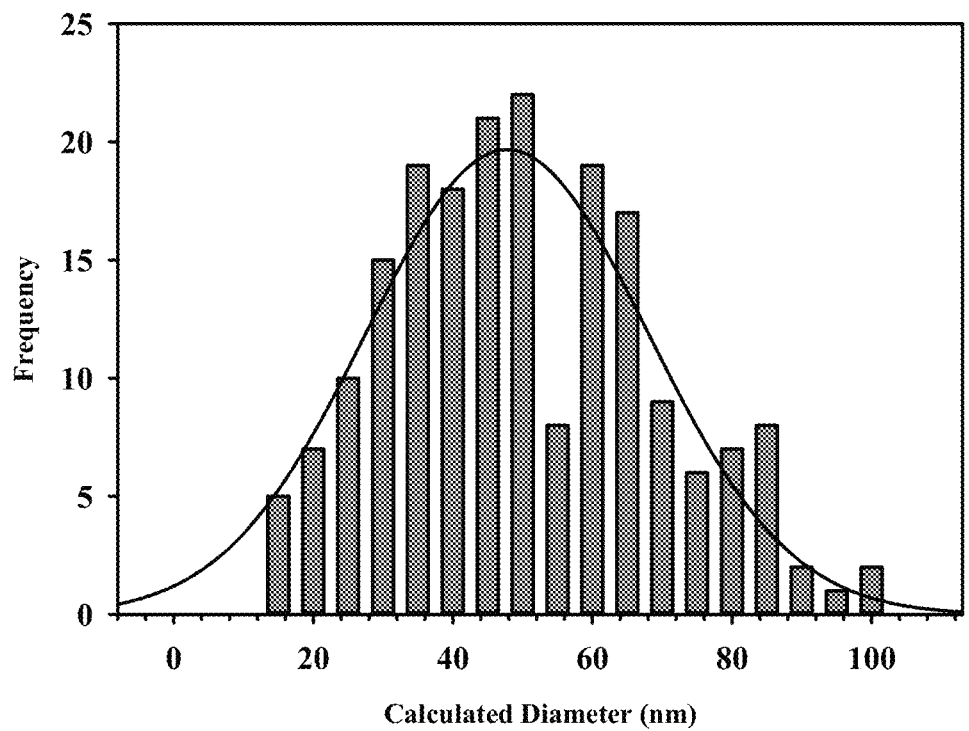

FIG. 10—Number-average particle size distribution of P(DEAEMA-co-MAPA-g-PEGMA) (PDETM30) generated by quantitative particle sizing from TEM micrographs. Distribution mean=47.9, std. dev.=19.6, n=197. Bars represent calculated data and line represents best fit Gaussian distribution ($R^2$=0.839).

Figure 11:
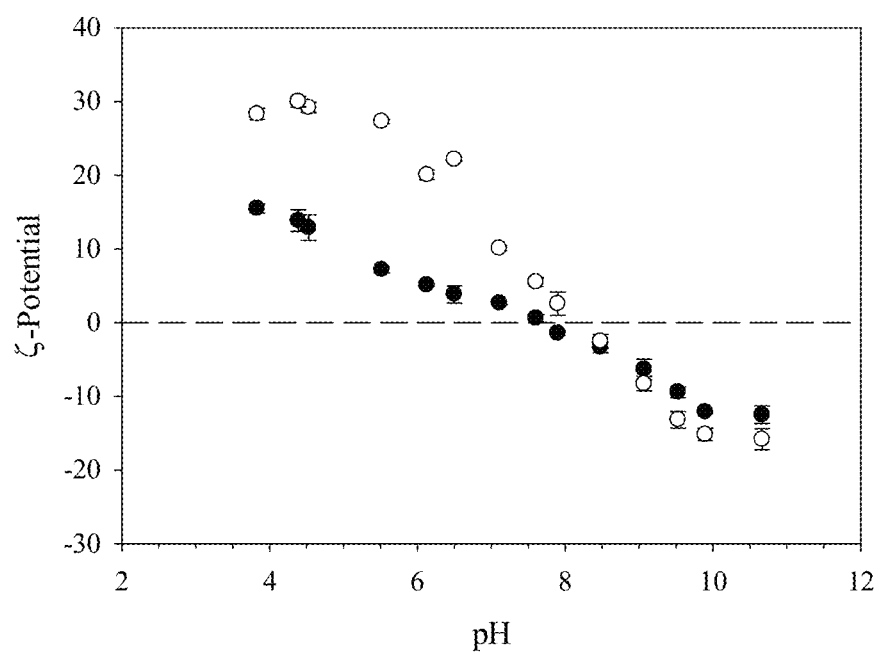

FIG. 11—Effective zeta-potential of P(DEAEMA-co-MAPA-g-PEG) PDETM30 (●) compared to P(DEAEMA-co-BMA-g-PEG) PDETB30 (○). Data points represent the mean of 3 sequential measurements±s.d.

Figure 12:
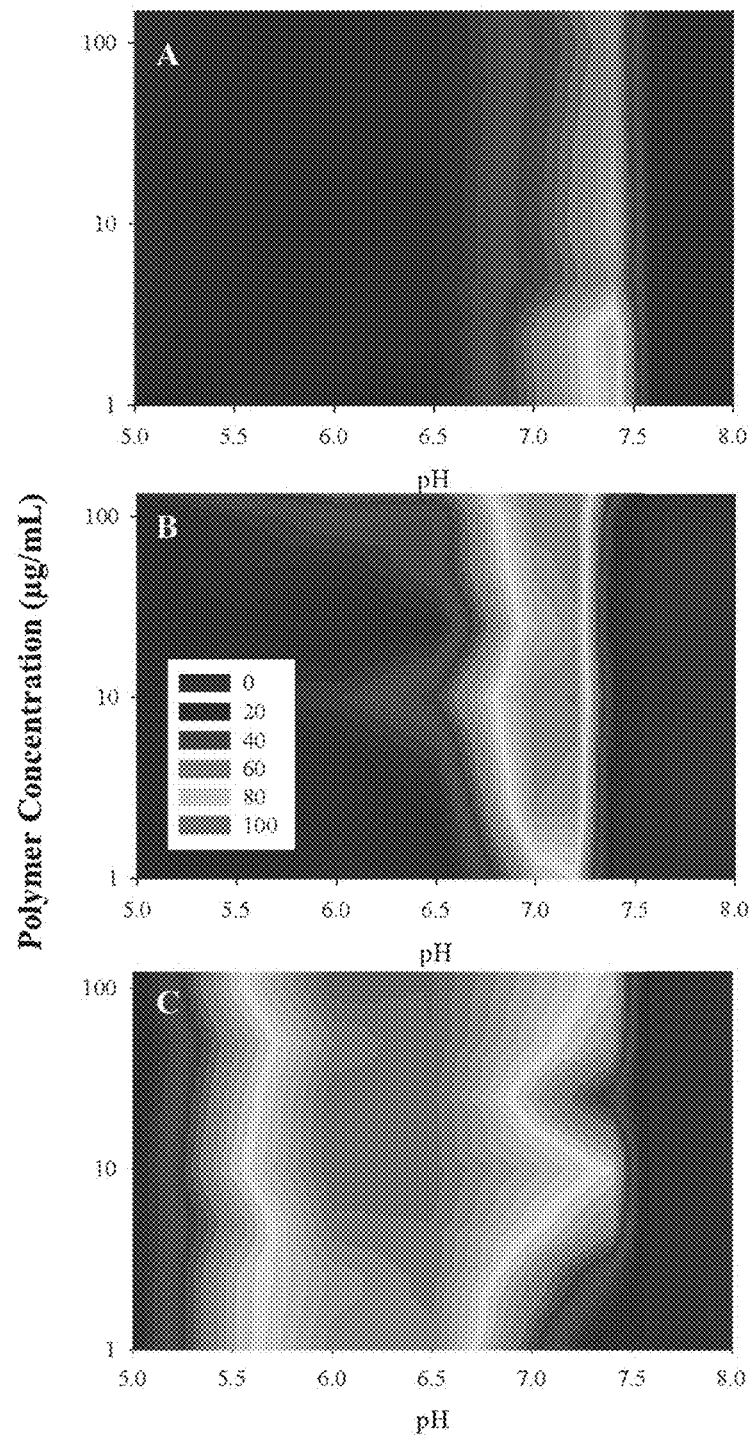

FIG. 12—Membrane-disruptive activity of pH-responsive nanogels PDET (A), PDETM30 (B), and PDETB30 (C). Sheep erythrocytes used as model membrane and hemoglobin release measured at λ=490 nm.

Figure 13:
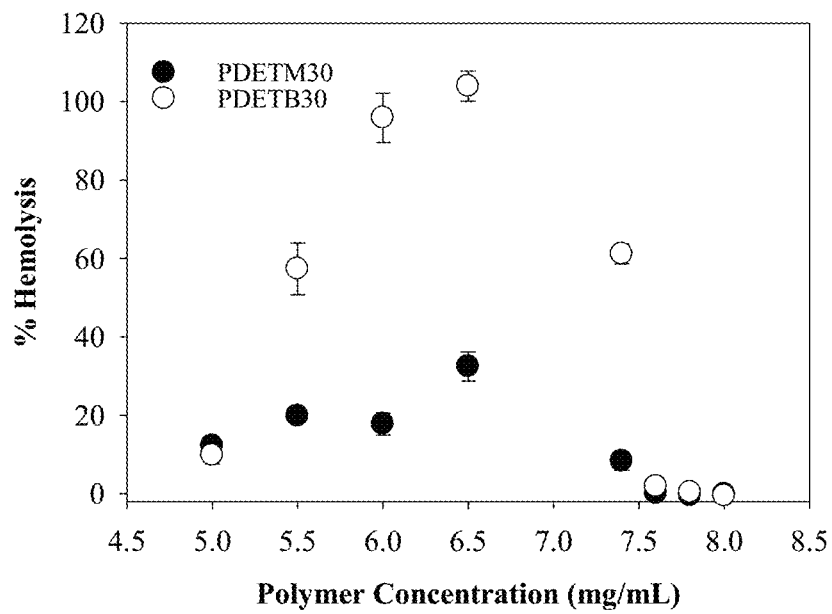

FIG. 13—Comparative hemolysis profile for PDETM30 (●) and PDETB30 (○) at 0.05 mg $mL^{-1}$. Data points represent the mean of a single experiment conducted in triplicate±standard deviation.

Figure 14:
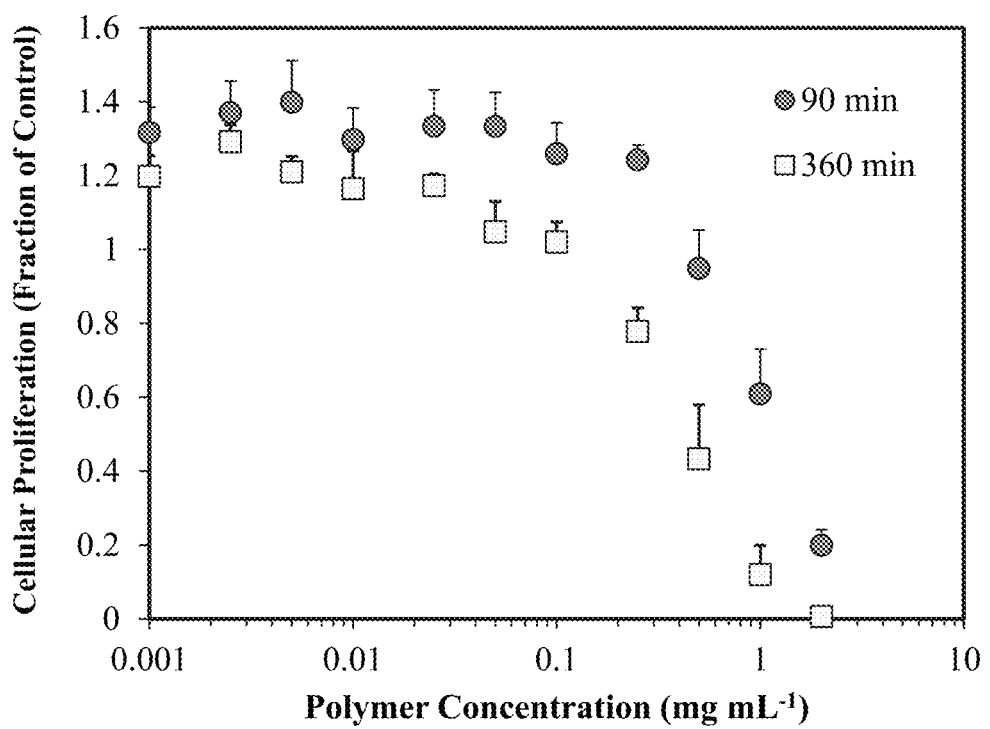

FIG. 14—Relative proliferation of Caco-2 cells upon exposure to P(DEAEMA-co-MAPA-g-PEG) (PDETM30) for 90 minutes (●) or 6 hours (□). The relative proliferation of Caco-2 cells was determined by MTS assay and is expressed as a fraction of the control (untreated) cells. Data are expressed as mean±SEM, n=4.

Figure 15:
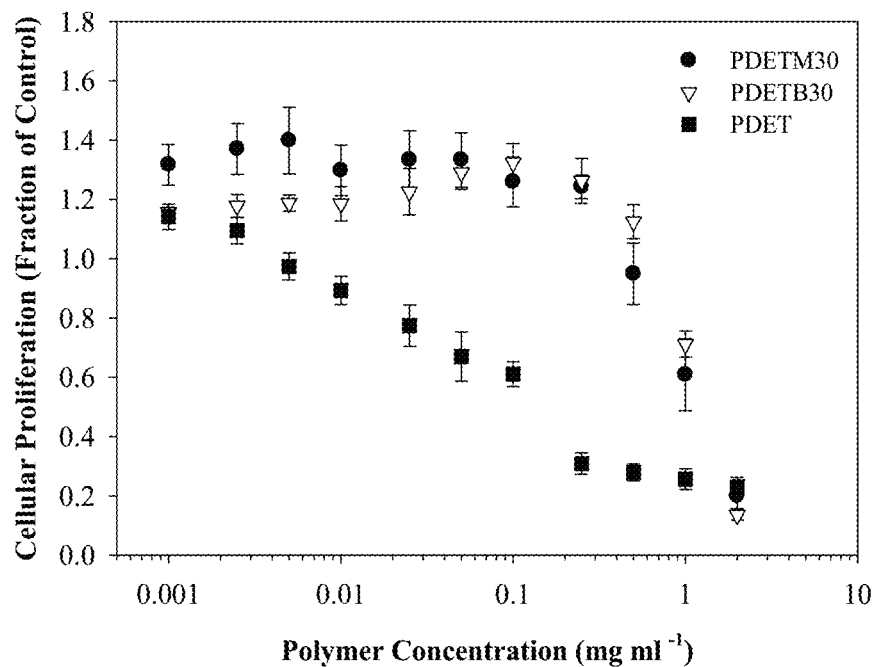

FIG. 15—Relative proliferation of Caco-2 cells upon exposure to PDETM30 (●), PDETB30 (▽), or PDET (□) for 90 min. The relative proliferation of RAW cells was determined by MTS assay and is expressed as a fraction of the control (untreated) cells. Data are expressed as mean±SEM, n=4.

Figure 16:
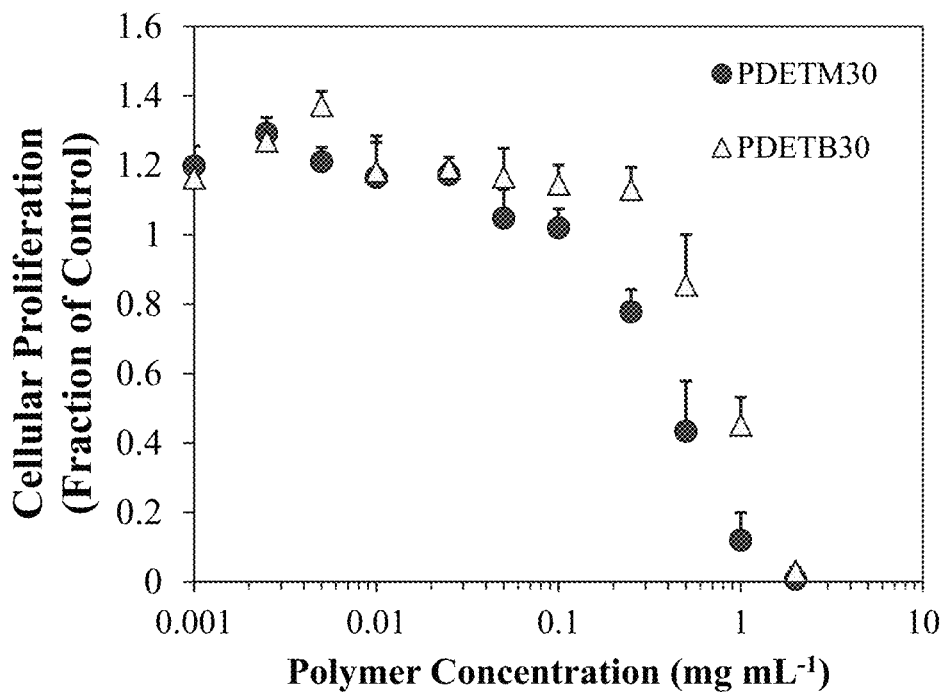

FIG. 16—Relative proliferation of Caco-2 cells upon exposure to PDETM30 (●) or PDETB30 (Δ) for 360 min. The relative proliferation of Caco-2 cells was determined by MTS assay and is expressed as a fraction of the control (untreated) cells. Data are expressed as mean±SEM, n=4.

Figure 17:
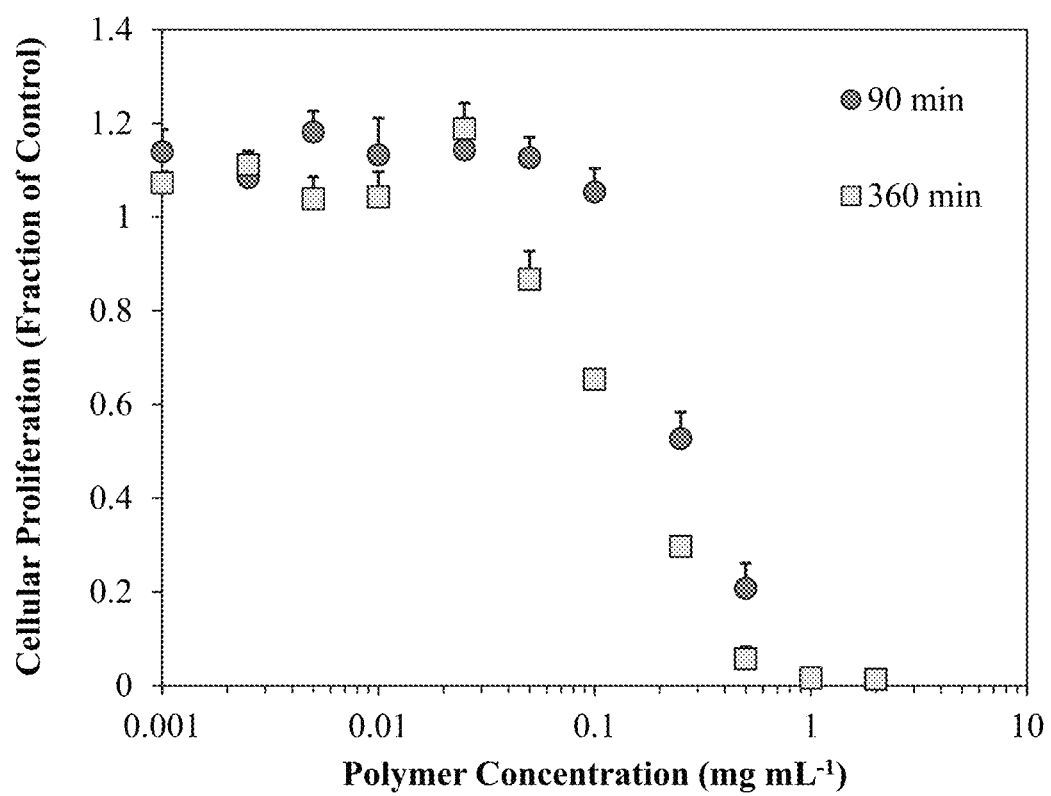

FIG. 17—Relative proliferation of RAW 264.7 cells upon exposure to P(DEAEMA-co-MAPA-g-PEG) (PDETM30) for 90 minutes (●) or 6 hours (□). The relative proliferation of RAW cells was determined by MTS assay and is expressed as a fraction of the control (untreated) cells. Data are expressed as means±SEM, n=4.

Figure 18:
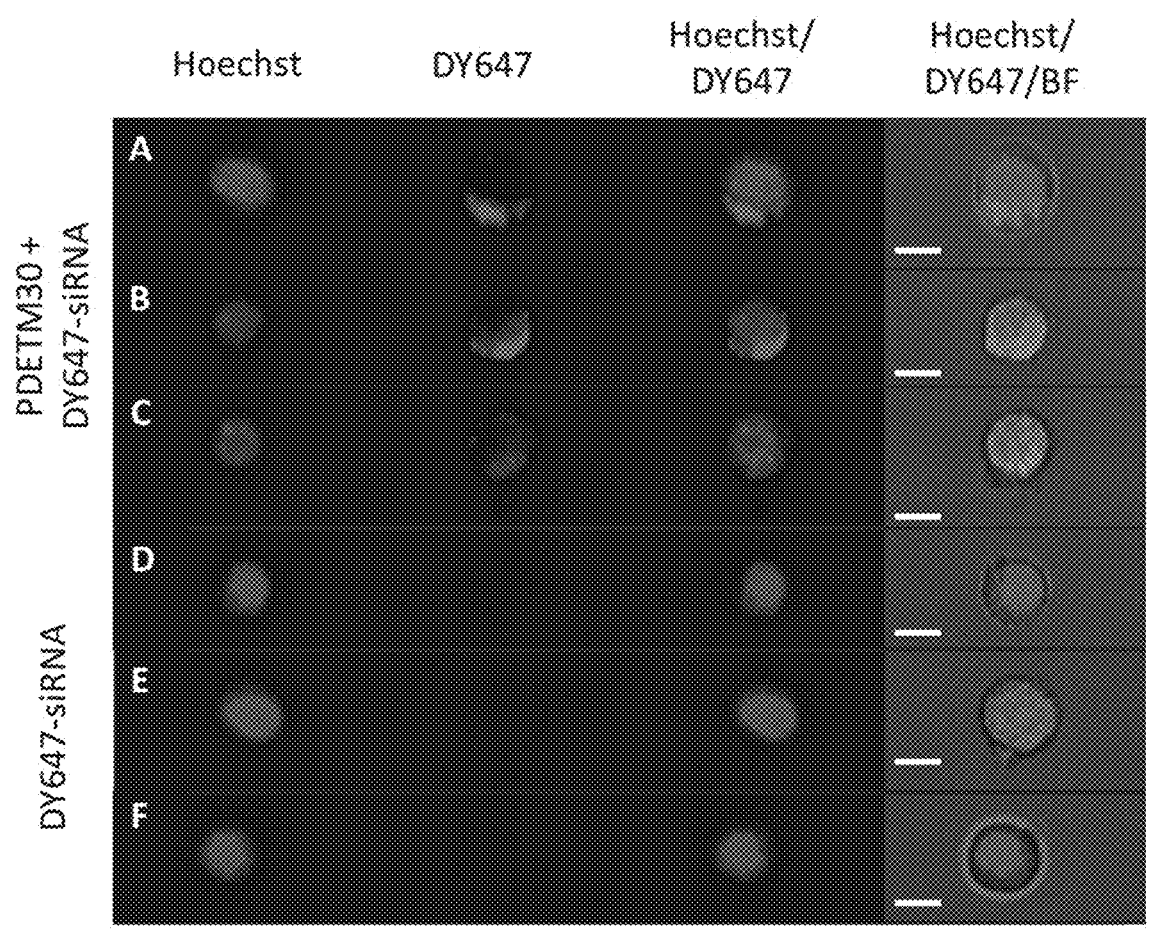

FIG. 18—DY647-siRNA delivery to RAW 264.7 cells. Nuclear stain (Hoechst 33342) shown in blue and DY647-siRNA (DyLight 647) shown in red. Two representative examples of RAW 264.7 cells exposed to PDETM30/DY647-siRNA (A-C) or DY647-siRNA alone (D-F) are shown. Scale bar represents 7 μm.

Figure 19:
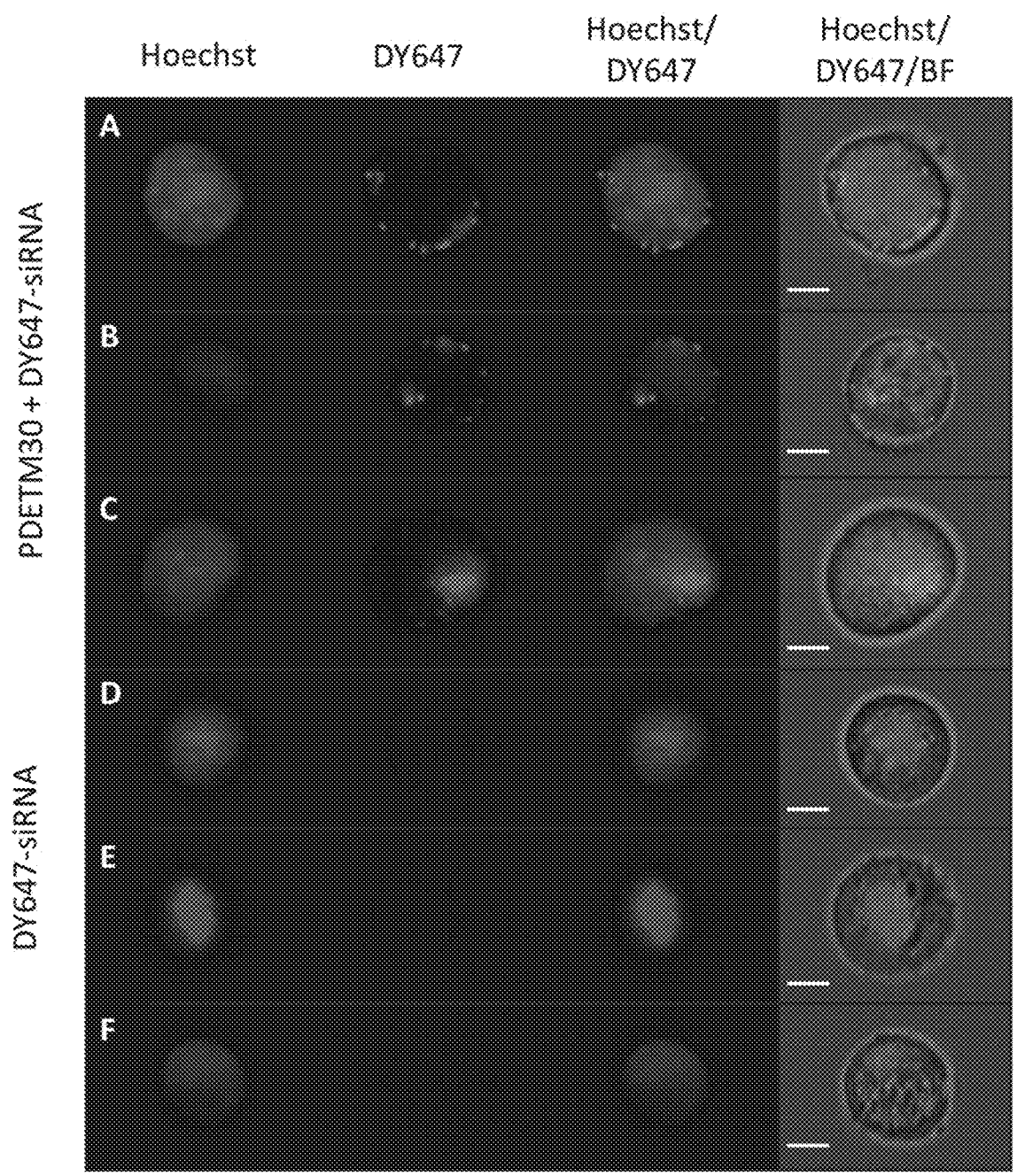

FIG. 19—DY647-siRNA delivery to Caco-2 cells. Nuclear stain (Hoechst 33342) shown in blue and DY647-siRNA (DyLight 647) shown in red. Three representative examples of Caco-2 cells exposed to PDETM30/DY647-siRNA (A-C) or DY647-siRNA alone (D-F) are shown. Scale bar represents 7 μm.

Figure 20:
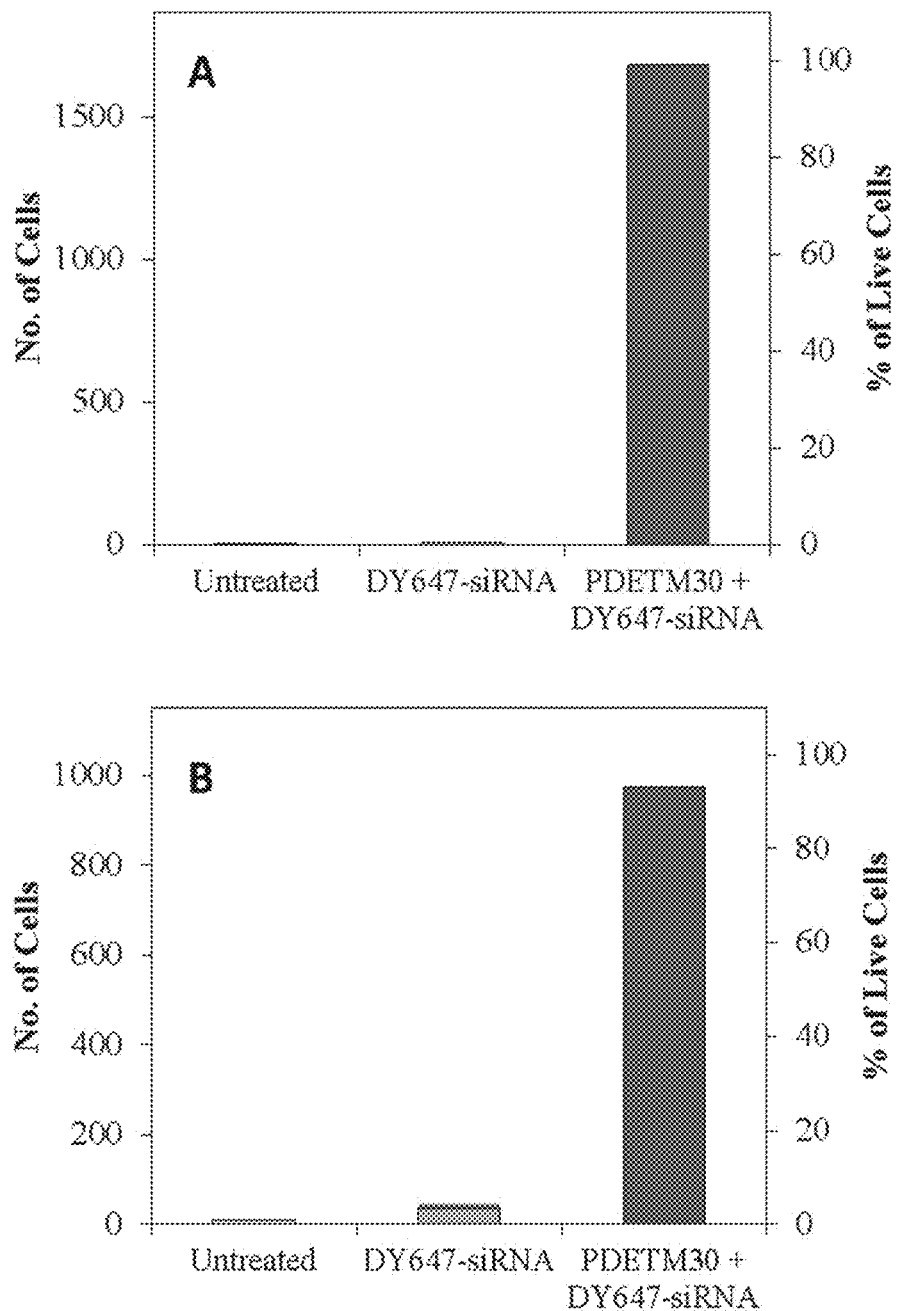

FIG. 20—Number (left axis) and proportion (right axis) of live cells with internalized DY647-siRNA. Untreated cells (gray), cells exposed to 100 nM DY647-siRNA alone (blue) or 100 nM DY647-siRNA+25 μg $ml^{-1}$ PDETM30

(red) in RAW 264.7 cells (A) and Caco-2 cells (B). Data represent pooled fractions from two independent experiments.

Figure 21:
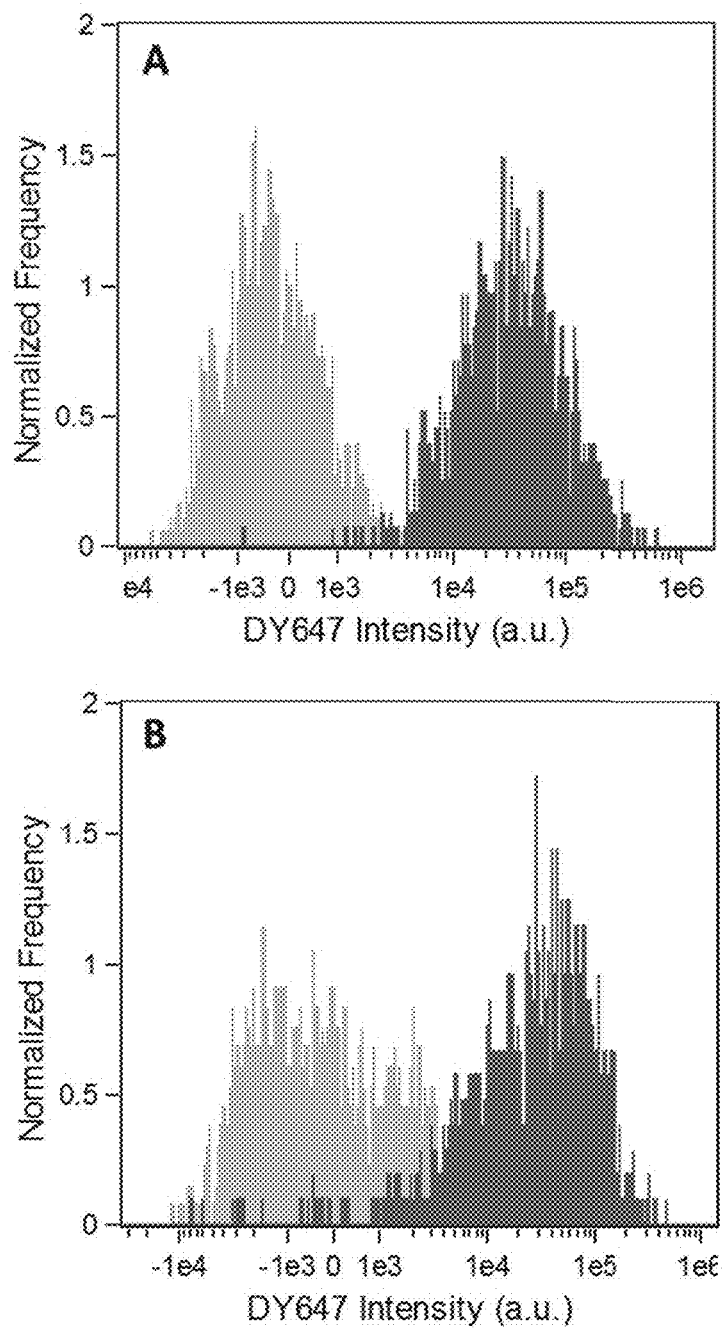

FIG. 21—Fluorescence intensity of DY647-siRNA in RAW 264.7 cells (A) and Caco-2 cells (B). Fluorescence histograms generated from cells exposed to DY647-siRNA alone (blue) or PDETM30/DY647-siRNA (red). Data represent pooled fractions from two independent experiments.

Figure 22:
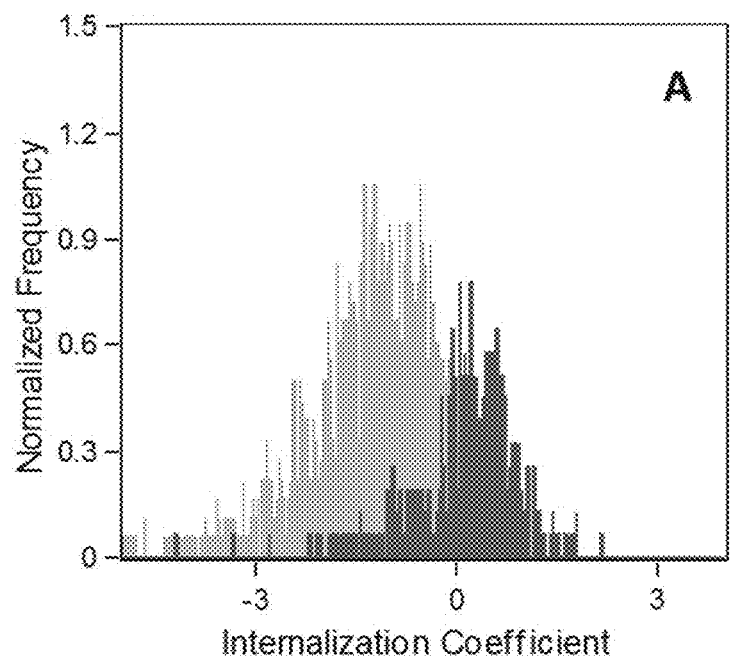
Figure 22:
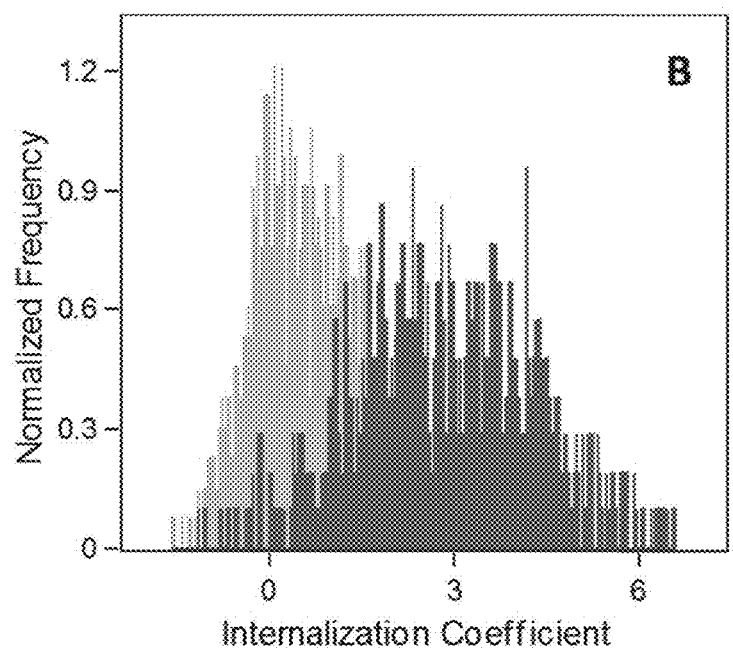

FIG. 22—Internalization coefficient of DY647-siRNA in RAW 264.7 cells (A) and Caco-2 cells (B). Histograms generated from image analysis of cells exposed to DY647-siRNA alone (blue) or PDETM30/DY647-siRNA (red). Data represent pooled fractions from two independent experiments.

Figure 23:
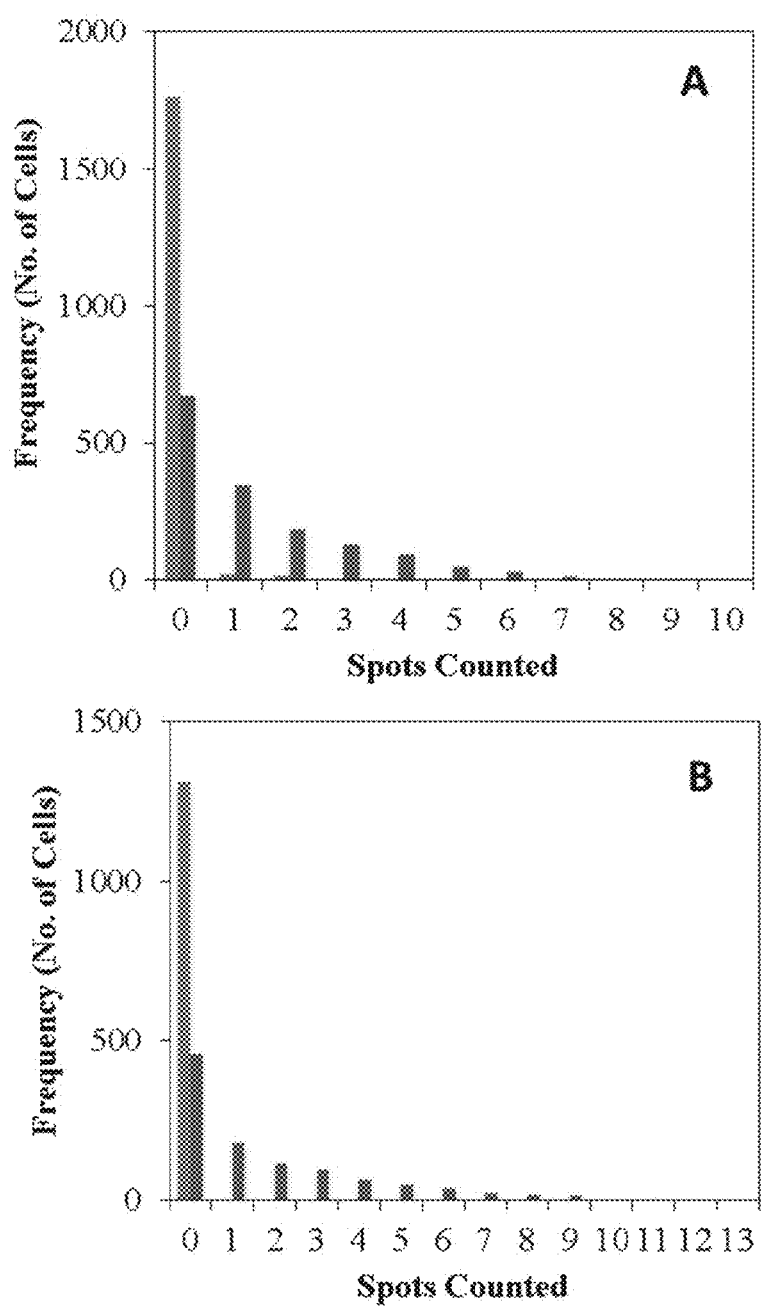

FIG. 23—Intracellular texture, or spot counting, of DY647-siRNA in RAW 264.7 cells (A) and Caco-2 cells (B). Histograms generated from image analysis of cells exposed to DY647-siRNA alone (blue) or PDETM30/DY647-siRNA (red). Data represent pooled fractions from two independent experiments.

While the present disclosure is susceptible to various modifications and alternative forms, specific example embodiments have been shown in the figures and are described in more detail below. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to compositions useful in the delivery of anionic therapeutic agents. More particularly, in some embodiments, the present disclosure relates to nanoscale, pH-responsive polycationic networks useful for the delivery of anionic biologic therapeutics and associated methods.

The present disclosure provides, according to certain embodiments pH-responsive polycationic hydrogels formed from a cationic monomer, a methacrylamide-derivatized hydrophobic amino acid moiety (also referred to as hydrophobic comonomer), and a crosslinker. Such hydrogels form random copolymers. The pH-responsive polycationic hydrogels undergo a volume phase transition in response to changing pH. The pH-responsive polycationic hydrogels of the present disclosure are methacrylate-based hydrogels. The hydrogels also may comprise PEG molecules at least partially disposed on an exterior surface of the hydrogel. The pH-responsive polycationic hydrogels are capable of swelling and deswelling in response to a change in pH. Accordingly, such hydrogels may be used to deliver, and may further comprise, anionic therapeutics such as, for example, anionic biologics like siRNA.

In operation, an anionic therapeutic may be included within the polymer network of the pH-responsive polycationic hydrogels, which also may be capable of enhancing cellular internalization. For example, at physiological pH (~7.4) a pH-responsive polycationic hydrogel may exist in a collapsed state thereby trapping an anionic therapeutic within a polymer network. When the pH-responsive polycationic hydrogel is introduced into a lower pH environment, such as, for example, within an endosome of a cell, the polymer network swells allowing release of the anionic therapeutic (e.g., siRNA, microRNA, and DNA).

In certain embodiments, the pH-responsive polycationic hydrogels of the present disclosure are cytocompatible (e.g., >80% at 100 ug/mL), have a size suitable for cellular delivery (e.g., 20-200 nm), are capable of binding nucleic acids (e.g., RNA binding >5 wt %), have a positive surface charge at pH ~7.4, have pH response that is tunable (e.g., collapsed at pH 7.4 and swollen at pH 5.5-6.5), and lower cell membrane disruption at pH ~7.4 and higher cell membrane disruption at pH <~7.

In general, suitable cationic monomers contain ionizable tertiary amine groups. By way of explanation, protonation of the tertiary amine group causes swelling by recruiting mobile counterions and increasing osmotic pressure in the hydrogel; and, electrostatic repulsion of neighboring amine groups also contributes to this volume phase transition. Examples of suitable cationic monomers include tertiary amino methacrylates, dimethyl amino ethyl methacralyates, diethyl amino ethyl methacralyates, diisopropyl amino ethyl methacralyates, morpholino ethyl methacrylates, polylysine methacrylates. Other suitable cationic monomers include 2-(diethylamino)ethyl methacrylate (DEAEMA) and 2-(tert-butylamino)ethyl methacrylate (BAEMA). The cationic content must be optimized to permit binding of anionic biomolecules (e.g. siRNA, miRNA) while avoiding undue toxicity to excess cationic content. The cationic monomers will typically comprise between about 50 and about 80 mol % of the hydrogel formulation.

Excess cationic content in polymer delivery systems can have deleterious effects. High cationic charge density is frequently correlated with toxicity. Accordingly, the hydrogels of the present disclosure also include a methacrylamide-derivatized hydrophobic amino acid moiety (e.g., to improve cytocompatibility and polymer-induced membrane destabilization). The hydrophobic moiety modulates the physiochemical properties of the hydrogel by altering the relative strength between polymer-polymer interactions and polymer-solvent-ion interactions. In this fashion, increasing hydrophobic content of pH-responsive polycationic hydrogels increases the strength of polymer-polymer interactions and favors a deswollen (collapsed) conformation. A consequence of this effect is a requisite increase in the ionization energy (e.g. lower pH) required to favor polymer-solvent-ion interactions and induce osmotic swelling of the polycationic hydrogel. As hydrophobic content increases, greater proton activity or greater ionization (i.e. lower pH) is required to promote polymer/solvent/ion interaction over polymer/polymer interaction. As expected, this effect also leads to a decrease in the onset of pH-dependent gel swelling. Therefore, the chemical nature and composition of the hydrophobic moiety may be tailored to tune the pH response of the pH-responsive polycationic hydrogels.

The critical pH required to induce a pH-dependent, hydrophobic to hydrophilic transition can be tuned according to the type and composition of hydrophobic moiety in the nansocale hydrogels. Hydrophobic comonomers in the hydrogel serve to promote polymer-polymer interactions and decrease the critical swelling pH necessary for osmotic gel swelling. These polycationic hydrogels are able to destabilize biological membranes most efficiently at or near their critical swelling pH. Hydrophobic moieties are used to match the hydrogel critical swelling pH with endosomal pH (pH ~6.5-7.0) to facilitate endsomal escape of the encapsulated cargo. Additionally, increasing hydrophobic moiety concentration in the polycationic hydrogel decreases cationic charge density. Cationic charge density is commonly associated with cellular toxicity, an unacceptable property in polymeric drug delivery systems. In these polycationic hydrogels, decreasing charge density leads to reduced non-specific toxicity in model cell lines.

The methacrylamide-derivatized hydrophobic amino acid should be capable of copolymerizing with the cationic polymer. Examples of suitable hydrophobic amino acids include alanine, isoleucine, leucine, valine, phenylalanine, tryptophan, tyrosine, methionine, and cysteine. In certain embodiments, the methacrylamide-derivatized hydrophobic amino acid is a methacrylamide-derivatized phenylalanine; for example, N-methacryloyl L-phenylalanine methyl ester (MAPA). The amount of hydrophobic moiety should be sufficient to decrease critical swelling pH while permitting hydrogel ionization and volume phase transition. In general, the amount of hydrophobic moiety will be from about 20% to about 50 mol %. In certain embodiments, the amount of hydrophobic moiety will be 20, 25, 30, 35, 40, 45, or 50 mol %.

In general the amount of cationic monomer and hydrophobic moiety may be adjusted to achieve the desired properties. By way of explanation, the inclusion of progressively higher amounts of hydrophobic moiety shifts the hydrophobic-hydrophilic transition downward to lower pH values. This is because a more hydrophobic network will experience higher van der Waals forces and will consequently require greater ionization energy (in the form of more protons) to induce a phase conformation. In general, suitable ratios of cationic monomer to hydrophobic moiety are from about 20% to about 50%. In certain embodiments, the ratios of cationic monomer to hydrophobic moiety is 20%, 25%, 30%, 35%, 40%, 45%, or 50%.

The pH-responsive polycationic hydrogels also include a crosslinker. The crosslinker helps create the polymer network by connecting polymer chains through covalent bonds. Such crosslinking also provides mechanical integrity to the resultant hydrogels. In general, suitable crosslinkers are capable of covalently linking polycationic polymers. Suitable crosslinkers may be homobifunctional (both ends are same) methacrylate crosslinkers such as, for example, ethylene glycol dimethacrylate (EGDMA), tetra(ethylene glycol) dimethacrylate (TEGDMA), and poly(ethylene glycol) dimethacrylate (PEGDMA), or combinations thereof.

The amount of crosslinker or density of crosslinking may vary depending on the average pore size desired. Increasing the crosslinking density results in hydrogels with smaller average pore sizes. Thus, the average pore size may be optimized for a particular anionic biologic therapeutics be delivered. In general, the average pore size should be large enough to permit delivery of a chosen anionic biologic therapeutic, but small enough to prevent substantial diffusion of the chosen anionic biologic therapeutics out of the hydrogel when the hydrogel is in a collapsed state. In general, the amount of crosslinker may range from about 0.5 to 5 mol % of the hydrogel. In certain embodiments, the crosslinker is 0.5, 1, 2, 3, 4, or 5 mol %.

In certain embodiments, the crosslinker may be degradable and thereby provide pH-responsive polycationic hydrogels that are degradable. In such embodiments, the crosslinker is at least partially disrupted (e.g., covalent bonds broken) by conditions within a cell. For example, the crosslinker may be chemically degraded by enzymes present within the cell. Examples of suitable degradable crosslinkers include, homobifunctional disulfide crosslinkers such as, for example, bis(2-methacryloyloxyethyl) disulfide (SSXL).

In certain embodiments, the pH-responsive polycationic hydrogels may have a size suitable for delivery into a cell. In certain embodiments, the pH-responsive polycationic hydrogels may have a z-average particle size diameter from about 20 nm to about 200 nm. In certain embodiments, the pH-responsive polycationic hydrogels may have a z-average particle size diameter from about 90 nm to about 100 nm. In specific embodiments, the pH-responsive polycationic hydrogels in a collapsed state may have a z-average particle size diameter from about 20 nm to about 100 nm. In specific embodiments, the pH-responsive polycationic hydrogels in a swollen state may have a z-average particle size diameter from about 100 nm to about 200 nm. In certain embodiments, the dry hydrogel has a number-average particle size diameter of from about 40 nm to about 80 nm. In certain specific embodiments, the dry hydrogel has a number-average particle size diameter of from about 50 nm.

As noted above, the pH-responsive polycationic hydrogels of the present disclosure also may comprise poly(ethylene glycol) (PEG) or polyoxazoline (POZ) polymers at least partially disposed on an exterior surface of the hydrogel. By way of explanation, PEG may provide improved biocompatibility to the hydrogel, as well as colloidal stability. The PEG is covalently attached to the cationic polymer's backbone. Suitable PEG/POZ include those having a molecular weight of from 1,000 Da to 10,000 Da; for example, 1,000-5,000 Da, 5,000-8,000 Da, 8,000-10,000 Da. Examples of suitable PEG molecules include, but are not limited to PEG having functional anhydride esters, heterobifunctional PEG, poly(ethylene glycol) methyl ether methacrylate (PEGMA), and polyoxazoline polymers with methyl (PMOZ), ethyl (PEOZ), and propyl (PPOZ) pendant groups, or combinations thereof.

In one embodiment, the pH-responsive polycationic hydrogel is P(DEAEMA-co-MAPA-g-PEGMA), where PEGMA is poly(ethylene glycol) methyl ether methacrylate, DEAEMA is 2-(diethylamino) ethyl methacrylate, and MAPA is N-methacryloyl L-phenylalanine methyl ester.

The pH-responsive polycationic hydrogels of the present disclosure may be synthesized via UV-initiated, oil-in-water photoemulsion polymerization.

In certain embodiments, the pH-responsive polycationic hydrogels provide a protective encapsulation and the mechanical integrity and chemical stability required to facilitate local delivery to a target site in the gastrointestinal tract. In such cases, the change in pH may arise, for example, from exposure to gastric fluids such as stomach or intestinal fluids. In certain embodiments, the polycationic networks are specifically designed for delivery to disease sites along the gastrointestinal tract, with potential utility in Crohn's disease, ulcerative colitis, celiac disease, and gastrointestinal carcinomas. Other potential uses for this technology encompass any biological therapeutic possessing a slight negative charge. This includes, but is not limited to proteins, plasmid DNA, microRNA, and short hairpin RNA.

To facilitate a better understanding of the present invention, the following examples of certain aspects of some embodiments are given. In no way should the following examples be read to limit, or define, the entire scope of the invention.

EXAMPLES

To investigate whether a phenylalanine moiety can impart hydrophobicity to P(DEAEMA-g-PEGMA) nanoscale hydrogels while enhancing relative biocompatibility, a methacrylamide-derivatized phenylalanine was synthesized. This functional monomer, N-methacryloyl L-phenylalanine methyl ester (MAPA), has been used previously to increase the hydrophobicity of poly(hydroxyethyl methacrylate) P(HEMA) microparticles in hydrophobic interaction chromatography applications. The present example investigates the use of MAPA as a hydrophobic comonomer in pH-responsive nanoscale hydrogels for intracellular delivery of siRNA. The aqueous solution properties, membrane-disruptive properties, cytocompatibility, and siRNA delivery efficiency are evaluated. Where relevant, the in vitro and physciochemical properties are compared to the unmodified P(DEAEMA-g-PEGMA), PDET, or the best-performing P(DEAEMA-co-TBMA-g-PEGMA) analogue, PDETB30.

Materials and Methods

Materials.

L-phenylalanine methyl ester hydrochloride, anhydrous triethylamine, methacryloyl chloride, hexanes, 2-(diethylamino) ethyl methacrylate (DEAEMA), Tetra(ethylene glycol) dimethacrylate (TEGDMA), Poly(ethylene glycol) methyl ether methacrylate (PEGMA), Mn ~2080-50 wt % solution in H2O, myristyltrimethyl ammonium bromide (MyTAB) and diethylpyrocarbonate (DEPC) were purchased from Sigma-Aldrich (St. Louis, Mo.). Irgacure 2959 was donated by Ceiba Geigy (Tarrytown, N.Y.).

Sodium hydroxide solution (NaOH, 1N), hydrochloric acid solution (HCl, 1N), methylene chloride, basic alumina—300 mesh, sodium chloride (NaCl), disodium phosphate heptahydrate (Na2HPO4.7H2O) sodium phosphate monohydrate (NaH2PO4.H2O), sodium azide ($N_3$Na), and Thermo Scientific HyClone USDA Tested Fetal Bovine Serum (FBS) were purchased from Fisher Chemical (South Plainfield, N.J.). Brij-30 was purchased from Acros Organics (Fair Lawn, N.J.).

Dulbecco's Modified Eagles Medium (DMEM) with 4500 mg $L^{-1}$ gluocose and sodium bicarbonate, without L-glutamine and sodium pyruvate, were obtained from Sigma-Aldrich (St. Louis, Mo.). Phosphate buffered saline (PBS) without calcium and magnesium and 200 mM L-glutamine solution were purchased from MediaTech (Manassas, Va.). CellTiter 96® AQueous Non-Radioactive Cell Proliferation Assay (MTS) was purchased from Promega (Madison, Wis.). Cell scrapers for RAW264.7 cells were purchased from BD Falcon (Franklin Lakes, N.J.). Propidium Iodide (PI), 1 mg $mL^{-1}$ solution in water and RNAse Free water were purchased from Life Technologies (Grand Island, N.Y.).

Unless otherwise specified, the water used in these experiments was purified by a Millipore Milli-Q Plus to a volume resistivity of 18.2 MΩ·cm.

MAPA Synthesis and Purification.

The reaction was conducted as follows: The reactive free base of L-phenylalanine methyl ester hydrochloride was extracted by dissolving the solid L-phenylalanine methyl ester hydrochloride in 1 N NaOH and extracting with methylene chloride. The resulting solution was chilled to 0° C. and 2 molar equivalents anhydrous triethylamine were added. Methacryloyl chloride was added dropwise to the mixing solution under nitrogen. The purge continued with stirring for 4 hours, after which the reaction mixture was sealed and allowed to react overnight at room temperature. The reaction mixture was purified by successive equivolume washes of 1 N HCl, saturated NaHCO3, and saturated NaCl. The organic phase was concentrated using rotary evaporation and purified using a Companion Automated Flash Chromatography Instrument (Teledyne-Isco, Lincoln, Nebr.) equipped with a 100 g silica column. Column was equilibrated with 500 ml hexanes, purification run length was set to 50 min with a solvent flow rate of 35 ml min-1. The solvent gradient was established as follows: Solvent A—hexanes, Solvent B—ethyl acetate. The gradient was adjusted from 0-40% B over 25 minutes and held for 10 minutes, then 40%-100% B over 10 minutes. Fractions of interest were determined by monitoring absorbance at 258 nm. The fractions were pooled and concentrated by rotary evaporation to yield a viscous, clear liquid. Subsequent drying in a vacuum oven produced a crystalline, white powder of N-methacryloyl L-phenylalanine methyl ester (MAPA). The chemical structure and molecular weight were verified using $^1$H-NMR and Mass Spectrometry, respectively.

Polymer Synthesis.

Hydrogel particles of nanoscale dimensions were synthesized via UV-initiated free radical photoemulsion polymerization/crosslinking according to previous reports from our laboratory. Briefly, DEAEMA and TEGDMA were passed through a column of basic alumina powder to remove inhibitor prior to use. MAPA was synthesized as described. Poly(ethylene glycol) methyl ether methacrylate (PEGMA), Mn ~2080 was used as received. DEAMA, TEGDMA, and MAPA were added to an aqueous solution containing 5 wt % PEGMA, Irgacure 2959 at 0.5 wt % of total monomer, 4 mg $mL^{-1}$ Brij-30 and ionic surfactant MyTAB. The mixture was emulsified using a Misonix Ultrasonicator (Misonix, Inc., Newtown, Conn.). The emulsion was purged with nitrogen gas and exposed to a UV source for 2.5 hr with constant stirring.

Polymer Purification.

During the initial stages of purification, we attempted the polyelectrolyte-ionomer purification method. However, the initial polymer-ionomer collapse and centrifugation of the reaction mixture resulted in a highly turbid, acetone-rich supernatant. After decanting the supernatant, the amount of remaining flocculated ionomer was uncharacteristically low and did not resuspend well in 0.5 N HCl. Thus, further purification efforts focused on the turbid supernants from purification cycles 1 and 2. These fractions were pooled and cooled to −80° C. in 50 ml centrifuge tubes. Following 24 h at −80° C., the supernatant stratified into a clear acetone-rich phase and semi-solid, turbid aqueous phase. The organic phase was carefully decanted and the remaining aqueous layer was again frozen at −80° C. for 24 h. Following additional decanting of the organic phase, the aqueous layer was transferred to 12-14 kDa MWCO Regenerated Cellulose Dialysis tubing (Spectrum Labs, Rancho Dominguez, Calif.). Polymer particles were dialyzed against ultrapure water for 7 days with the water changed twice daily. Following dialysis, polymers were flash frozen in liquid $N_2$ and lyophilized for 5 days.

$^1$H-NMR Spectroscopy.

The composition of crosslinked PDETM30 was investigated using a Varian (Palo Alto, Calif.) DirectDrive 400 MHz nuclear magnetic resonance spectrometer equipped with automatic sampler. Deuterium oxide ($D_2O$, 99.9%) was obtained from Cambridge Isotope Laboratories (Andover, Mass.). Deuterium chloride (DCI, 100.0%) was obtained from Acros Organics (Fairlawn, N.J.). All glassware, including NMR Tubes (Wilmad Lab Glass, Vineland, N.J.), 2 mL sample vials, and Pasteur pipettes were dried overnight in a vacuum oven. Polymer samples of approximately 40 mg were weighed directly in sample vials and $D_2O$ was added to bring the final polymer concentration to 20 mg $mL^{-1}$. Samples were briefly sonicated in a sonic bath and transferred to NMR tubes for subsequent analysis. All NMR Spectra were analyzed using SpinWorks 3™ software.

Dynamic Light Scattering Analysis.

Measurements of the z-average particle size were collected at 25° C. using a Malvern Zetasizer NanoZS (Malvern Instruments Corp., Malvern, UK) operating with a 633 nm laser source equipped with MPT-2 Autotitrator. DLS measurements of particle size and pH-responsive behavior were conducted by resuspending lyophilized particles in PBS at 0.5 mg mL$^{-1}$. The suspension pH was adjusted to 10.5 using 1 N NaOH and gradually lowered to pH 3.5 using 1 N HCl. Measurements of the z-average particle size were collected at 25° C. and pH intervals of 0.5.

Transmission Electron Microscopy.

Transmission electron micrographs were collected using a FEI Tecnai (Hillsboro, Oreg.) Transmission Electron Microscope (80 kV) at magnifications from 16,500× to 160,000×. Lyophilized particles were diluted in ddH$_2$O and stained with 2% uranyl acetate immediately prior to imaging. Typically, 5 µL of 0.02 w/v % of particle suspension was dropped onto a 400-mesh Formvar-coated copper TEM grid (Electron Microscopy Sciences, Hatfield, Pa.) and excess liquid wicked off using filter paper. An equivalent volume of 2 w/v % uranyl acetate was then added to the grid and allowed to stain for 60 seconds before excess liquid was wicked away with filter paper. Particle volume in the dry state was taken as the cube of mean diameter from TEM images. Particle diameters were calculated from the particle area as determined by an ImageJ particle sizing algorithm. Reported values represent the mean±standard deviation (n>50).

Electrophoretic Light Scattering.

Measurements of the effective surface charge were collected 25° C. using a Malvern Zetasizer NanoZS (Malvern Instruments Corp., Malvern, UK) operating with a 633 nm laser source equipped with MPT-2 Autotitrator. Measurements of ζ-potential as a function of pH were conducted by resuspending lyophilized particles in 5 mM phosphate buffer at 0.5 mg mL$^{-1}$. The suspension pH was adjusted to 10.5 using 1 N NaOH and gradually lowered to pH 3.5 using 1 N HCl. Electrophoretic light scattering measurements of the surface ζ-potential were collected at 25° C. with nanogels suspended in 5 mM sodium phosphate.

Hemolysis Assays.

Sheep blood in sodium citrate was obtained from Hemostat Laboratories (Dixon, Calif.) and used for up to two weeks after receipt. Phosphate buffers (0.15 M) from pH 5.0-8.0 were prepared by dissolving predetermined amounts of monosodium phosphate and disodium phosphate in ultrapure DI water. The buffer pH was adjusted as needed using 1 N HCl or 1 N NaOH. Dry nanoscale hydrogels were suspended in 150 mM phosphate buffer at the desired pH at a concentration of 2.5 mg ml$^{-1}$ and allowed to equilibrate overnight. Erythrocytes were isolated from whole sheep blood by 3 successive washes with freshly prepared 150 mM NaCl. Red blood cells (RBCs) were separated by centrifugation from 10 minutes at 2,000×g. The supernatant and remaining buffy coat were carefully aspirated and discarded. After removing the supernatant following the final wash, RBCs were suspended in a volume of 150 mM phosphate buffer identical to that of the original blood aliquot at the pH matching that of the suspended polymers. This solution was diluted 10-fold in 150 mM phosphate buffer to yield an RBC suspension of approximately 5×10$^8$ cells/mL. In a typical experiment, 1×10$^8$ RBCs were exposed to polymer concentrations from 1 µg mL$^{-1}$-2 mg mL$^{-1}$ while shaking in a bead bath (LabArmor, Cornelius, Oreg.) pre-equilibrated at 37° C. Following a 60 min incubation period, samples were centrifuged at 14,500 RPM for 5 min to separate cells and membrane fragments. An aliquot of each sample was transferred to a clear 96-well plate and hemoglobin absorbance was measured at 541 nm. Negative controls (0% lysis) consisted of 150 mM phosphate buffer at experimental pH and positive controls (100% lysis) consisted of RBCs incubated in ultrapure DI water.

Cell Culture.

Human colorectal adenocarcinoma cells (Caco-2) and murine macrophages (RAW 264.7) were maintained in Dulbecco's Modified Eagles Medium (DMEM) supplemented with 100 U mL$^{-1}$ penicillin, 100 µg mL$^{-1}$ streptomycin, and 10% fetal bovine serum (FBS) (Complete DMEM). Caco-2 cells were used between passage 34 and 62. RAW 264.7 cells were used between passage 9 and 17. Caco-2 cells were passaged by washing with pre-warmed Dulbecco's phosphate buffered saline (DPBS) and subsequent incubation with 0.25% Trypsin-EDTA at 37° C. Trypsin was neutralized by addition of fresh, prewarmed DMEM and cells were separated by centrifugation. The resulting pellet was suspended in 10 mL DMEM and cell count was determined using a Scepter Automated Cell Counter (Millipore, Billerica, Mass.) with 60 µm tips. The cell suspension was diluted as necessary and added to tissue-culture treated flasks or multi-well plates. Caco-2 cells were typically passaged at 1:5 ratio with media replenished every 2-3 days. RAW 264.7 cells were passaged by washing with prewarmed DPBS and replacing the original culture volume with fresh DMEM. Cells were removed from the flask surface by gentle scraping with a 25 cm cell scraper. The number of suspended cells was counted using a Scepter Automated Cell Counter and diluted as necessary for addition to tissue culture flasks or multi-well plates. RAW 264.7 cells were typically passaged every 2 days.

Cytocompatibility Studies.

In vitro cytocompatibility was determined for polycationic nanoscale hydrogel networks using commercially available cytotoxicity assays. MTS assays were performed using the CellTiter 96 AQueous One Solution Cell Proliferation Assay kit in which the soluble tetrazolium salt [3-[4,5-dimethylthiazol-2-yl]-5-(3-carboxymethoxyphenyl)-2-(4-sulfophenyl)-2H-tetrazolium] (MTS) is reduced to a purple formazan product. The absorbance of the formazan product is proportional to the number of viable cells. Stock solutions of polymer were suspended in PBS and allowed to equilibrate overnight. Caco-2 cells were seeded in 96-well plates at 10,000 cells/well and incubated for 36 hours prior in 200 µL DMEM. RAW 264.7 cells were seeded in 96-well plates at 10,000 cells/well and incubated for 36 hours prior to assay in 200 µL DMEM. Media was aspirated and cells were washed 1× with DPBS and incubated in 160 µL serum-free DMEM for 30 minutes. Following this incubation period, polymer stock solutions at 5× were added to cells for designated exposure times.

Following the exposure period (90 min or 360 min), media and polymer were aspirated and replaced with a DMEM/MTS solution. Absorbance at 490 nm was recorded after 4 hours or 90 min incubation in the DMEM/MTS solution for Caco-2 and RAW, respectively.

siRNA Complexation.

RNA complexation buffer was prepared by dissolving 3.15 g sodium phosphate dibasic heptahydrate, 0.02 g potassium phosphate monobasic monohydrate, 0.20 g potassium chloride, and 8.01 g sodium chloride in Milli-Q purified water. Following salt dissolution, the solution pH was adjusted to pH 5.50 using 1 N HCl and ultrapure water was added to bring the final solution volume to 100 mL. To remove nucleases, diethylpyrocarbonate (DEPC) was added at 0.1% and incubated at room temperature overnight. The buffer solution was then autoclaved to remove DEPC. Polymer-siRNA complexes were formed by combining aqueous solutions of PDETM30, siRNA, 10× RNAse-free PBS, and RNAse-free water to obtain desired concentrations. Typically, complexation was allowed to commence for 60 min and polymer-siRNA were complexed at a 10:1-20:1 ratio (g polymer/g siRNA).

siRNA Internalization.

DyLight 647-labeled small interfering RNA (Sense: DY647-UAAGGCUAUGAAGAGAUACUU) (SEQ ID NO: 1) was purchased from Thermo Scientific (Lafayette, Colo.). (P(DEAEMA-co-MAPA-g-PEGMA) (PDETM30) was synthesized and purified as described herein. Flow cytometry buffer was prepared by combining FBS, DPBS, and $N_3Na$ to form 1% FBS and 0.1% $N_3Na$ in DPBS.

Concentrated suspensions (20×) of PDETM30, PDETM30/DY647-siRNA, or DY647-siRNA were prepared to contain 0.5 mg $mL^{-1}$ PDETM30, 26.5 µg $mL^{-1}$ (~2000 nM) DY647-siRNA, 1× complexation buffer, and RNAse free $H_2O$. Control samples (PDETM30 only, DY647-siRNA only) were prepared in a similar fashion, replacing the volume of the absent component(s) with RNAse free $H_2O$.

RAW 264.7 cells or Caco-2 cells were seeded at $1\times10^5$ cells/well and allowed to grow to 80% confluence before exposure. Immediately prior to exposure to PDETM30/DY647-siRNA, cells were washed 1× with 2 mL DPBS and media was replaced with 1.9 mL serum-free DMEM. Concentrated suspensions of PDETM30, PDETM30/DY647-siRNA, or DY647-siRNA were added to wells in 100 µL increments and allowed to incubate with cells for 60 min in a 37° C., 5% $CO_2$ atmosphere. Following this incubation period, cells were rinsed 3×DPBS (with calcium and magnesium) and the media was replaced with 2 mL serum-free DMEM. Hoechst 33342 was added to each well for nuclear staining at a final concentration of 2.5 µg $ml^{-1}$. The nuclear staining process was completed for 30 min for RAW 264.7 cells and 45 min for Caco-2 cells at 37° C., 5% $CO_2$. Following Hoechst incubation, cells were rinsed 3× with DPBS (w/out calcium and magnesium).

RAW 264.7 cells were isolated by replacing the final DPBS wash with 1 mL flow cytometry buffer and gently scraping the cells. Cell suspensions from each well were transferred to microfuge tubes and centrifuged for 5 min at 500×g. The supernatant was discarded and cell pellet re-suspended in 100 µL flow cytometry buffer.

Caco-2 cells were isolated by replacing the final DPBS wash with 500 µL 0.25% trypsin-EDTA and incubating at 37° C., 5% $CO_2$ for 8 min. Trypsin was neutralized by adding 3 mL DMEM with 10% FBS and without phenol red. Cell suspensions were centrifuged for 5 min at 500×g. The supernatant was discarded and cell pellet re-suspended in 100 µL flow cytometry buffer. All cell suspensions were kept on ice until use. Propidium iodide (PI) was used as a live/dead discriminator and was added to cell suspensions immediately before analysis at a final concentration of 1 ng $mL^{-1}$.

Analysis of cellular internalization was conducted using an Amnis ImageStream (Seattle, Wash.) imaging flow cytometer equipped with lasers at 405 nm, 488 nm, 658 nm, and 785 nm. Fluorescent data were collected using Channel 1 (430-505 nm, Hoechst), Channel 4 (595-660 nm, PI), Channel 5 (660-745 nm, DY647), and Channel 6 (745-800 nm, side scatter). Cells were imaged with a 60× objective. Fluid velocity was set to a nominal value of 40 mm/sec. Fluorescent compensation matrices were constructed using Amnis IDEAS® software and verified manually for proper fit. At least 5,000 cells were collected for analysis. Dead cells (PI positive) were excluded from analysis. Out-of-focus cells were also excluded from further analysis by gating the Gradient RMS feature in IDEAS® software. This feature detects image sharpness by calculating large changes in pixel values across the brightfield image. Typically, cells with Gradient RMS value <40 were considered out of focus.

Results and Discussion

MAPA Synthesis and Purification.

The acrylation of L-phenylalanine methyl ester (L-PhME) was performed according the to the reaction scheme in FIG. 2. The methyl ester analogue of L-phenylalanine was chosen to avoid side reactions with unprotected carboxylate group of L-phenylalanine. Initially, the hydrochloride salt of L-PhME was added to cold (4° C.) dichloromethane (DCM). However, after a short period of stirring, the entire mixture turned to a cloudy solid, likely due to chemical incompatibility between the DCM solvent and the salt form of L-PhME. To isolate the free base of L-PhME, approximately 200 mL of 1N NaOH was added to the solid organic mixture and agitated briefly. The entire mixture was transferred to a separatory funnel and inverted several times. After settling, the DCM phase was collected and saved (Extract fraction 1). The remaining basic aqueous fraction was washed twice more with approximately 65 mL of DCM (Extract fractions 2 and 3). A final organic wash with 65 mL DCM was accompanied by the addition of 9 g of NaCl to the basic aqueous phase (Extract fraction 4). Subsequent $^1$H-NMR and thin layer chromatography (TLC) analysis revealed the vast majority of L-PhME partitioned into the organic phase during the first DCM wash (Extract fraction 1). The remaining extract fractions contained quantities of L-PhME barely perceptible by $^1$H-NMR. Therefore, Extract fraction 1 was concentrated via rotary evaporation and used as described herein.

Following preliminary purification and concentration via partial rotary evaporation, the reaction product mixture consisted of a viscous liquid. Exhaustive rotary evaporation led to a crystallization of white solid on the flask walls. Thus, sufficient DCM was left in the flask to maintain the reaction product in solution. Column chromatography proceeded in 3 successive runs with approximately 1 mL of viscous reaction product added to the column per run. A sample chromatogram from the flash chromatography is shown in FIG. 3.

The $^1$H-NMR spectrum of the purified MAPA product is shown in FIG. 4 and peak assignments and relative areas in Table 1. The peak areas match the expected proton ratios and the spectrum corresponds well with published reports. The high-resolution mass spectrum (not shown) also confirms successful synthesis and isolation of the intended product. The mass spectrum shows the presence of one peak at 248 Da, corresponding to the MZ+ fragment. The expected molecular weight of MAPA is 247 Da. The MAPA monomer exhibits long-term stability when stored dry at 4° C. Additional mass spectroscopy studies revealed no loss of structural fidelity following 18 months of storage under these conditions (data not shown).

TABLE 1

Peak assignments and relative integration values of the $^1$H-NMR spectrum of purified N-methacryloyl L-phenylalanine methyl ester (MAPA) monomer

| Peak Assignment | δ (ppm) | Protons | Integration Value |
|---|---|---|---|
| A | 7.05-7.30 | 5, R—$C_6H_5$ | 5.416 |
| B | 6.10-6.28 | 1, R—NH—R | 1.082 |
| C | 5.60-5.70 | 1, R—C=$CH_2$ | 1.046 |
| D | 5.30-5.40 | 1, R—C=$CH_2$ | 1.049 |
| E | 4.85-5.00 | 1, $R_2$—CH—NH—R | 1.105 |

TABLE 1-continued

Peak assignments and relative integration values of the $^1$H-NMR spectrum of purified N-methacryloyl L-phenylalanine methyl ester (MAPA) monomer

| Peak Assignment | δ (ppm) | Protons | Integration Value |
|---|---|---|---|
| F | 3.65-3.85 | 3, —O—CH$_3$ | 3.000 |
| G | 3.12-3.28 | 2, Ph—CH$_2$—R | 2.101 |
| H | 1.85-2.03 | 3, R—CH$_3$ | 3.010 |

Polymer Synthesis and Purification.

The nanogel purification process employed in this study is distinctly different than our previous reports. In contrast to all other previous formulations, the P(DEAEMA-co-MAPA-g-PEGMA) (PDETM30) nanogels did not flocculate or sediment following the acetone-induced polyelectrolyte-polymer transition (described in the inventors application WO 2014059430 A1, the entirety of which is incorporated by reference). Rather, the supernatant from purification cycle 1 was a milky, slightly translucent solution. The centrifuged pellet, normally a white mass, was much smaller and less densely packed than typically observed. The supernatants from all tubes were then pooled and placed in a −80° C. freezer to undergo fractional freezing purification. After 24 hours, the supernatants had phase-separated into a clear, acetone-rich organic phase, a hazy interface layer, and a white, quasi-solid, water-rich aqueous phase. The organic layer, and any dissolved unreacted monomers or surfactant unimers, was carefully decanted and discarded. The remaining quasi-solid thawed to a turbid, white liquid solution within minutes, suggesting a low freezing temperature and considerable acetone content. This solution was subjected to another round of fractional freezing with similar phase separation observed after 24 h at −80° C. Following removal of the clear, acetone-rich phase, the turbid aqueous fraction dialyzed extensively to remove acetone, unreacted monomers, and surfactants.

$^1$H-NMR Spectroscopy.

The proton NMR spectrum (FIG. 6) corresponds well with the $^1$H-NMR spectra of crosslinked P(DEAEMA-co-BMA-g-PEGMA) in D$_2$O as seen in the inventors application WO 2014059430 A1, the entirety of which is incorporated by reference. The oxyethylene protons (—O—CH$_2$—CH$_2$—) from grafted PEGMA are evident in a strong peak at δ=3.6 ppm and the terminal methoxy protons (—O—CH$_3$) from grafted PEGMA are visible at δ=3.3 ppm. The inset spectra also confirm the presence of MAPA and DEAEMA functional groups in the polymer. The left inset shows the aromatic protons from MAPA at δ=7.2-7.4 ppm. The right inset shows the ethylamino (—CH$_2$—CH$_3$)$_2$ protons from DEAEMA at approximately δ=1.25 ppm.

Identification of residual surfactant is somewhat problematic in the spectra of this crosslinked polymer nanogel. The primary surfactant used during synthesis, Brij-30, displays prominent peaks in chemical shift regions near or overlapping with the PEGMA (δ~3.6 ppm) or DEAEMA (δ~1.2 ppm) peaks. Other minor peaks exist in the $^1$H-NMR spectra of Brij-30, such as that of the etheric protons bridging the tetraethylene glycol portion and dodecane portion of Brij-30 (—O—CH$_2$—CH$_2$—C$_{10}$H$_{21}$). These protons are visible at δ=3.445 ppm and δ=1.58 ppm in CDCl$_3$. No distinct peaks are observed near these chemical shifts in FIG. 6. Also, the terminal hydroxyl group of Brij-30 demonstrates a chemical shift of δ~2.8 ppm in organic solvents like CDCl$_3$. However, this peak is not expected to appear in D$_2$O due to the rapid exchange rate with surrounding hydrogen or deuterium. In practice, the $^1$H-NMR spectra of neat solutions of Brij-30 result in sharp, well-defined peaks at the expected chemical shift. The spectrum in FIG. 6 does not contain any such peaks and those present near δ=3.6 ppm and δ=1.2 ppm are characteristically broad, in accordance with the previous work (described in the inventors application WO 2014059430 A1, the entirety of which is incorporated by reference) of polymer NMR. From these observations, it appears the fractional freezing and dialysis purification was sufficient to remove Brij-30 from PDETM30.

A conclusive determination about the presence or absence of MyTAB was also problematic. In part, the polyelectrolyte-ionomer flocculation and sedimentation was designed to expel the cationic surfactant MyTAB through electrostatic repulsion. As this formulation did not undergo the polyelectrolyte-ionomer purification, the presence of residual MyTAB may be expected. A small, sharp peak around δ=3.1 ppm may correspond to the methyl protons on the quarternized amino group of MyTAB. $^1$H-NMR analysis of neat MyTAB in DMSO-d$_6$ reveals strong peaks near δ=3.08 ppm (9 protons) and δ=1.28 ppm (24 protons).

Compared to the area of the PEGMA methoxy protons (Peak c, FIG. 6), the peak at δ=3.1 ppm has relative molar ratio between these two groups can be estimated by:

$$\frac{n_{MyTAB}}{n_{PEGMA}} = \frac{A_{MyTAB,3.1}/9}{A_{PEGMA,3.3}/3} \quad (1)$$

where $A_{MyTAB,3.1}$ is the integrated area of the putative methyl protons adjacent to the quarternized amine of MyTAB, 9 is the number of equivalent protons associated with this peak, $A_{PEGMA3.3}$ is the integrated area of the terminal methoxy group of PEGMA, and 3 is the number of equivalent protons. Thus, the estimated molar ratio of MyTAB to PEGMA is 0.061. Considering the nanogels are approximately 0.5 mol % PEGMA (according to the inventors application WO 2014059430 A1, the entirety of which is incorporated by reference), the approximate molar ratio of MyTAB to PDETM30 is ~3×10$^{-4}$. This suggests that MyTAB, if present, is present only in a very small proportion.

Dynamic Light Scattering Analysis.

Dynamic light scattering was used to study the physicochemical properties of the PDETM30 nanogels, including size, swelling ratio, and critical swelling pH. The hydrodynamic diameter and polydispersity index reported represent those determined by Cumulants analysis as outlined in ISO 13321. FIG. 7 depicts representative intensity-weighted sized distributions of PDETM30 in the collapsed (pH 9) and swollen (pH 6) state. The existence of a single population suggests that the Cumulants method is appropriate for this analysis.

The z-average diameter and polydispersity are plotted as a function of pH in FIG. 8. The PDETM30 nanogels are significantly larger in aqueous suspension than analogous preparations with t-butyl methacrylate (TBMA). PDETM30 exhibits a collapsed diameter of approximately 150 nm. In contrast, PDETB30 exhibits a collapsed diameter of approximately 92 nm. Upon exposure to increasingly acidic conditions, PDTEM30 undergoes a phase conformation from collapsed hydrophobe to swollen hydrophile. This phase conformation results in a distinct change in volumetric swelling, the magnitude of which is driven by a balance between the free energy of polymer-solvent interactions, osmotic pressure generated by mobile counterions inside the gel, and elastic contractile response to gel deformation.

The critical swelling pH was determined to be $pH_c$=7.00. By comparison, the $pH_c$ of PDET and PDETB30 were measured at 7.37 and 6.65, respectively. Prior studies have demonstrated that increased network hydrophobicity leads to a decrease in the $pH_c$. Therefore, the network hydrophobicity imparted by the MAPA comonomer is intermediate relative the PDET (no comonomer) and PDETB30 (TBMA comonomer). The breadth of the phase transition, simply the pH difference between swollen and collapsed states, is approximately 0.9 pH units. The breadth of the phase transitions for PDET and PDETB30 are approximately 0.65 and 1.56, respectively.

The polydispersity index (PdI), is given by a ratio of the second ($\mu_2$) and first moment ($\Gamma$) of the Cumulants analysis ($\mu_2/\Gamma^2$) and describes the apparent width of the size distribution. Typically, with PdI in this manner, a PdI of <0.05 is considered monodisperse and a PdI of >0.7 is considered polydisperse. The PDETM30 nanogels have a narrow size distribution in aqueous suspension; the PdI was estimated at 0.10-0.12 throughout the measurement. In contrast, nearly all other syntheses resulted in nanogels with PdI ~0.18-0.22.

Transmission Electron Microscopy.

The dry diameter of PDETM30 nanogels was determined to be 47.9±19.6 nm by transmission electron microscopy (TEM). The diameter was calculated by determining the particle area in ImageJ® and calculating the corresponding circular diameter. Images acquired at 26,500× and 43,000× were used to construct a number-average particle size distribution. Representative TEM micrographs are shown in FIG. 9 and the calculated number-average particle size distribution in FIG. 10. The TEM micrographs reveal circular particles, which corresponds to a roughly spherical morphology. Moreover, the dry particle mean size and size distribution correspond well with those determined for TBMA and TBAEMA nanogels (described in the inventors application WO 2014059430 A1, the entirety of which is incorporated by reference).

Electrophoretic Light Scattering.

Measurements of the ζ-potential were performed to evaluate the colloidal stability and effective surface charge in response to dynamic pH. The ζ-potential of PDETM30 is compared to the TMBA analogue, PDETB30, in FIG. 11. Similar to the other copolymer nanogels described in the inventors application WO 2014059430 A1, the entirety of which is incorporated by reference, PDETM30 possess a reversible surface charge and isoelectric point (IEP) ~7.67. The surface charge is slightly positive at physiological pH, ζ-potential ~1.22 mV. The maximum ζ-potential at pH 3.5 is approximately 16 mV. In contrast, the maximum ζ-potential for PDETB30 at pH 3.5 is approximately 28 mV. A potential reason for this disparity may be an increase in the PEG graft density on PDETM30 and therefore an increase in charge shielding by the PEG corona. Evidence from the $^1$H-NMR spectra of crosslinked nanogels in DCl in support this assertion (see the inventors application WO 2014059430 A1, the entirety of which is incorporated by reference). Comparing the relative areas between PEGMA protons and DEAEMA protons in a given copolymer gives a semi-quantitative estimate of the relative prevalence of PEGMA on the surface of the nanogel. This estimate, for the ratio of PDETM30 to PDETB30, yields a value of 4.45, suggesting that PDETM30 has a higher proportion of PEGMA to DEAEMA than does PDETB30. This method of estimation is only semi-quantitative, however, in that significant signal attenuation occurs in the $^1$H-NMR analysis of crosslinked polymer networks. The nanogel interior, even in the swollen state, is a likely a highly viscous network of polymer chains. Therefore, this comparative method likely underestimates the DEAEMA content and overestimates the PEGMA content. There is also a possibility that PDETM30 contains identical PEGMA content to PDETB30 and simply a lower molar proportion of DEAEMA. This result is not likely, given the nature and extent of the pH-responsive transition observed by DLS in FIG. 8. Further investigations to quantify the ionizable amine content via acid titration are currently underway to more conclusively address this question.

Hemolysis Assays.

The membrane-disruptive properties of PDETM30 were investigated using the hemolysis assay described in WO 2014059430 A1, the entirety of which is incorporated by reference. These studies serve to provide insight on the combinations of pH values and concentrations at which the nanogels are most able to destabilize lipid bilayers. These studies are shown to be a rapid screen to approximate endosomolytic ability of synthetic polymer for intracellular drug delivery.

The pH values tested in this analysis range from pH 5.0-pH 8.0; experiments performed at pH 5.00, 5.50, 6.00, 6.50, 7.00, 7.20, 7.40, 7.60, 7.80, and 8.00. The concentrations tested range from 1-100 μg ml$^{-1}$; with experiments performed with 100, 50, 25, 10, 5, 2.5, and 1 μg ml$^{-1}$ PDET, PDETM30 or PDETB30 suspended in 150 mM phosphate buffer at the specified pH.

The pH- and concentration-dependent hemolysis was determined according to Equation 2:

$$\% \ Hemolyis = \frac{A_{sample} - A_{blank}}{A_{max} - A_{blank}} \quad (2)$$

Where $A_{sample}$ represents RBCs exposed to polymer at a given pH and concentration, $A_{blank}$ is the absorbance of the supernatant after RBC exposure to phosphate buffer at a given pH, and $A_{max}$ represents maximum lysis following RBC exposure to DI water. The hemolytic ranges of PDET, PDETM30, and PDETB30 are shown on the contour plots in FIG. 12 and arranged in order of membrane-disruptive ability. There is a clear dependence of polymer composition on the ability to destabilize erythrocyte membranes. The trends for membrane destabilization mirror those observed in DLS analysis. The $pH_c$ values for these three copolymer formulations are 7.37 for PDET, 7.00 for PDETM30, and 6.65 for PDETB30. Moreover, the values for transition breadth ($pH_{swollen}$-$pH_{collapsed}$) are 0.65 for PDET, 0.9 for PDETM30, and 1.45 for PDETB30.

Notably, the pH range for maximum hemolysis follows a similar trend. PDET displays maximum hemolysis around pH 7.4-7.6; conditions that correspond to its determined $pH_c$. Similarly, PDETM displays maximum hemolysis around pH 6.5-7.2 and PDETB30 displays maximum hemolysis around pH 6.0-pH 7.0. These data suggest that the phase transition is critically important to modulate membrane-disruptive behavior. At pH values above the phase-transition, the collapsed nanogel may be well protected by PEG grafts and may not have sufficient exposed surface area to interact with, and destabilize, lipid bilayers. At pH values well below the phase transition, the swollen nanogel may be sufficiently ionized to mitigate any hydrophobic interactions between the exposed nanogel surface and the lipid bilayer of erythrocyte membranes. In the transition region, the partially-swollen nanogel may contain a heterogeneous mixture of ionized and hydrophobic segments. The partial ionization will permit osmotic swelling and the surface area of each nanogel will increase by a factor proportional to $d^2_{swollen}/d^2_{collapsed}$. This leads to a concomitant decrease in the surface PEG graft density and may permit increased hydrophobic association between the nanogel surface and lipid bilayers. The analysis of pyrene emission spectroscopy provides additional support for relationship between nanogel hydrophobicity and membrane-disruptive activity.

A comparative hemolysis profile for PDETB30 and PDETM30 is shown in FIG. 13. These data show the pH-dependent hemolysis at a single nanogel concentration (50 µg ml$^{-1}$). In practice, nanogels concentrations of 5-50 µg ml$^{-1}$ were used in transfection experiments. As seen in this comparison, PDETM30 is substantially less effective at erythrocyte disruption in the pH range (pH 5.50-6.50) expected in early endosomes. While PDETB30 demonstrates nearly 100% hemolysis at pH 6.50 and pH 6.00, PDETM30 demonstrates 32% and 20%, respectively. However, PDETM30 is relatively non-disruptive (~8% hemolysis) at physiological pH where PDETB30 demonstrates ~60% hemolysis at pH 7.4. This suggests that while PDETM30 is not as potent as the TMBA analogue PDETB30, it may have some utility in intracellular delivery applications, particularly as a mild membrane-destabilizing agent.

Cytocompatibility.

The influence of polymer composition on cytotoxicity was examined using a cellular proliferation assay. In this work, the polymer toxicity was inversely related to the ionizable amine content (i.e. nanogels containing less DEAEMA were less cytotoxic under tested conditions). The $LD_{50}$, or polymer dose that results 50% reduction in cellular metabolic activity, was estimated by fitting cytotoxicity data with a four parameter Hill model of the form:

$$y = y_0 + \frac{a \cdot x^b}{c^b + x^b} \quad (3)$$

Where y is the measured cellular proliferation (relative to untreated cells), $y_0$ is the background signal or lower asymptote, $a-y_0$ is the range for the fit, b is the slope of the response curve, and x is the polymer concentration (mg mL$^{-1}$) to which the cells were exposed for designated time points. This model is a typical dose-response curve commonly employed to model ligand-receptor binding and drug concentration-effects.

Based on the aqueous solution properties of PDETM30 discussed heretofore in the present disclosure and examples, it is expected that PDETM30 will exhibit cytotoxicity at intermediate levels relative to P(DEAEMA-g-PEGMA) (PDET) and P(DEAEMA-co-TMBA-g-PEGMA) (PDETB30).

Caco-2 Cells.

PDETM30 demonstrates both time- and concentration-dependent toxicity, as shown in FIG. 14. Exposure times of 90 minutes and 360 minutes were chosen to as liberal and conservative approximations for the mean intestinal transport time, estimated to be approximately 3-4 h in humans. According to the MTS assay, PDETM30 caused no decrease in cellular proliferation (relative to untreated control) in Caco-2 cells at concentrations up to 0.25 µg mL$^{-1}$ for 90 min exposure or 0.10 mg mL$^{-1}$ for 360 min exposure. The calculated $LD_{50}$ values for PDETM30 and Caco-2 cells are 1.18 mg mL$^{-1}$ for 90 min exposure and 0.43 mg mL$^{-1}$ for 360 min exposure.

PDETM30 displays comparable toxicity to PDETB30 and improved toxicity relative to PDET (FIG. 15). The similarity in toxicity profile of PDETM30 and PDETB30 can be seen in FIG. 15 for 90 min exposure and FIG. 16 for 360 min exposure. This result is expected based on the previous relationships between polymer composition, aqueous solution properties, and cytotoxicity developed in Sour previous work. Below concentrations of 0.25 mg mL$^{-1}$, both PDETM30 and PDETB30 display negligible toxicity. In fact, these nanogels appear to exert a stimulatory effect on the metabolic activity of Caco-2 cells under the test conditions. As expected from the ionizable amine density, PDET is considerably more toxic than the hydrophobically-modified nanogels PDETB30 and PDETM30.

RAW 264.7 Cells.

Similar the observations in Chapter 5, RAW 264.7 cells were categorically more sensitive to the presence of nanogels than were Caco-2 cells. The $LD_{50}$ for PDETM30 was estimated to be 0.27 mg mL$^{-1}$ for 90 min exposure and 0.14 mg mL$^{-1}$ for 360 min exposure (FIG. 17). The nature of this increase in toxicity can be ascribed to the phagocytic activity of the RAW macrophages. Whereas nanogels will be internalized through nonspecific uptake pathways in Caco-2 cells, there will be additional uptake from phagocytosis in RAW 264.7 cells. In all further studies examining cellular internalization of DY647-siRNA/PDETM30 complexes, PDETM30 was used at a concentration (0.025 mg mL$^{-1}$) well below the toxic thresholds for Caco-2 and RAW 264.7 cells.

siRNA Internalization.

Imaging flow cytometry was used to assess the ability of PDETM30 to facilitate the delivery of siRNA to model cell lines. This technique offers a powerful combination of qualitative visual evidence and quantitative statistical counting. In this analysis of siRNA internalization, imaging flow cytometry was used to investigate the proportion of siRNA positive cells and the relative quantity of siRNA uptake by comparing fluorescent intensity between DY647-siRNA/PDETM30-treated and untreated samples. Moreover, detailed image analysis comparing thousands of combined fluorescent and brightfield images permitted the assessment of cellular internalization (vs. surface adsorption) and intracellular texture.

As seen in the micrographs in FIG. 18, PDETM30 enables the cytoplasmic delivery of DY647-siRNA to RAW 264.7 cells. Cell nuclei are shown in blue (Hoechst) and siRNA in red (DY647). Panels A-C show representative images of cells exposed 25 µg mL$^{-1}$ PDETM30 and 100 nM DY647-siRNA for 60 minutes. Panels D-F show representative images of cells exposed only to 100 nM DY647-siRNA for 60 min. As expected due to its high MW (~13 kDa) and negative charge, little to no internalization was observed by the naked siRNA. Following complexation with PDEM30, the siRNA internalization increased substantially. Similar observations were made for Caco-2 cells exposed to PDETM30/DY647-siRNA or DY647-siRNA under identical conditions (FIG. 19).

FIG. 20 shows the total number (and proportion) of siRNA positive cells relative to untreated control. Cells were deemed siRNA positive by gating the entire Channel 5 (Em: 660-745 nm, DY647) fluorescent intensity histogram of an untreated control sample. Cells in this range of fluorescent intensity were considered siRNA negative. Cells with fluorescent intensity greater than this gated region were considered siRNA positive. As seen in FIG. 20, PDETM30 enables siRNA internalization in nearly 100% of RAW 264.7 cells (Panel A) and approximately 93% of Caco-2 cells (Panel B). As previously mentioned, only live cells with suitable brightfield focus were analyzed. This rapid and ubiquitous internalization is encouraging, particularly in the absence of any dedicated targeting ligands to promote internalization.

The fluorescent intensity histograms in FIG. 21 reveal that PDETM30 drastically increases the fluorescent signal of DY647-siRNA. These histograms compare populations exposed to DY647-siRNA alone (blue) or PDETM30/DY647-siRNA (red). In accordance with FIG. 20, these observations are consistent in both RAW 264.7 cells (FIG. 21, Panel A) and Caco-2 cells (FIG. 21, Panel B). The similarity in median fluorescence intensity between RAW 264.7 cells (~33,000) and Caco-2 cells (~30,000) suggests that phagocytosis, a mechanism of internalization in the RAW macrophages, does not account for a significant fraction of the internalized siRNA.

A major advantage of imaging flow cytometry is the ability to distinguish between intracellular and surface localization of fluorescent probes. Extensive rinsing of cells with PBS is typically employed prior to conventional flow cytometry; generally this is sufficient for the putative removal of surface-adsorbed ligands. In this analysis, the brightfield cell image and fluorescent siRNA image were compared to determine the extent of internalization, or internalization coefficient. This parameter is defined by the ratio of intensity inside the cell to the intensity of the entire cell, where inside the cell and entire cell are defined by masks created in the brightfield channel. Positive values for the internalization coefficient signify intracellular localization, while negative values signify membrane localization. Values near zero signify a mix of these two staining patterns.

As seen in FIG. 22, the median internalization coefficient is positive for both RAW 264.7 cells (Panel A) and Caco-2 cells (Panel B), indicating that PDETM30 facilitates intracellular delivery of DY647-siRNA to these two cell types. A similar analysis examined the colocalization of DY647-siRNA and cell nuclei stained with Hoechst 33342. As expected, there was no evidence for nuclear localization of DY647-siRNA.

FIG. 23 illustrates the distribution in intracellular spots of siRNA in RAW 264.7 cells and Caco-2 cells. Punctate staining patterns are typically associated with vesicular entrapment of fluorescently labeled molecules. A spot counting algorithm in IDEAS® software was used to determine the number of punctate spots in each live, focused cell. The spot mask was established to identify bright spots 3-2000 pixels in area. With a 60× objective, each pixel corresponds to 0.3 µm×0.3 µm. Therefore, the mask was able to identify punctate spots of approximately 0.58 µm-4.78 µm in diameter. Mature late endosomes have a diameter of 0.25-1 µm and lysosomal compartments can range from 0.5 nm-1.5 µnm. Thus, this method will not accurately account for all endolysosomal entrapment but can theoretically detect vesicular entrapment in some late endosomes and most lysosomes.

The spot count distributions in FIG. 23 suggest a diffuse staining pattern (few spots) of DY647-siRNA fluorescence rather than a punctate staining pattern (many spots). These distributions are in good agreement with the micrographs from FIG. 18 and FIG. 19, which show few distinct spots in the intracellular siRNA fluorescence. Given that over 90% of RAW 264.7 cells and Caco-2 cells contain detectable DY647-siRNA fluorescence, the lack of spots cannot be simply ascribed to a lack of internalization. These data suggest that PDETM30 is an efficient vehicle for enabling internalization and endosomal escape of siRNA.

CONCLUSIONS

A reactive phenylalanine derivative, N-methacryloyl L-phenylalanine methyl ester (MAPA) was successfully synthesized in order to modulate hydrophobicity and physicochemical properties of pH-responsive nanogels. The structure and molecular weight of the intended MAPA product were verified via $^1$H-NMR and mass spectroscopy, respectively. The MAPA monomer was used in a photoemulsion polymerization to create P(DEAEMA-co-MAPA-g-PEGMA) nanogels. These responsive polymer networks have a roughly spherical morphology and dry diameter of approximately 47 nm, as determined by TEM. These nanogels exhibit a volume phase transition from collapsed hydrophobe to swollen hydrophile around pH 7.0, as determined by DLS. DLS measurements also indicate a relatively narrow distribution of particle sizes with a z-average diameter of approximately 150 nm.

In many of the in vitro assays, PDETM30 displayed intermediate performance relative to unmodified nanogel PDET and the best performing TBMA-modified nanogel PDETB30. For comparison, relevant physical and in vitro properties of PDETM30 and PDETB30 are summarized in Table 2 and Table 3. In studies of membrane destabilization using sheep erythrocytes, PDETM30 was most disruptive at pH values proximal to its critical pH for phase transition. Relative to the PDET nanogels, PDETM30 was a more potent agent for membrane destabilization but was less effective than PDETB30. Similarly, PDETM30 demonstrates improved cytocompatibility relative to PDET and comparable cytocompatibility to PDETB30. Moreover, PDETM30 displays no overt toxicity to Caco-2 cells or RAW 264.7 cells at conventional transfection concentrations (<50 µg ml$^1$) for up to 6 h exposure.

TABLE 2

Physical properties of PDETM30 nanogels compared to PDETB30

| | Hydrophobic Monomer | $D_H$ at pH 8.0 (nm) | $D_H$ at pH 6.0 (nm) | ζ-Potential at pH 8.0 (mV) | ζ-Potential at pH 6.0 (mV) | Dry Diameter (nm) |
|---|---|---|---|---|---|---|
| PDETB30 | [tert-butyl methacrylate structure] | 93.4 | 121 | 2.6 ± 1.6 | 21.6 ± 0.7 | 50 ± 17 |

TABLE 2-continued

Physical properties of PDETM30 nanogels compared to PDETB30

| Hydrophobic Monomer | $D_H$ at pH 8.0 (nm) | $D_H$ at pH 6.0 (nm) | ζ-Potential at pH 8.0 (mV) | ζ-Potential at pH 6.0 (mV) | Dry Diameter (nm) |
|---|---|---|---|---|---|
| PDETM30 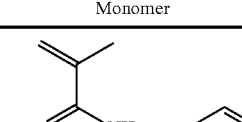 | 151.4 | 184.1 | −1.4 ± 0.3 | 5.12 ± 0.2 | 47.9 ± 19 |

TABLE 3

In vitro properties of PDETM30 compared to PDETB30

| Hydrophobic Monomer | Hemolysis at pH 7.4[1] (%) | Hemolysis at pH 6.5[1] (%) | $LD_{50}$ in RAW Cells[2] (mg ml$^{-1}$) | $LD_{50}$ in Caco-2 Cells[2] (mg ml$^{-1}$) | DY647-siRNA delivery[3] |
|---|---|---|---|---|---|
| PDETB30 | 61.1 ± 2.5 | 103.9 ± 3.8 | N/A | 1.23 | 1.2 × 10$^4$ |
| PDETM30 | 8.0 ± 0.2 | 32.4 ± 3.7 | 0.27 | 1.18 | 3.3 × 10$^4$ |

[1]Hemolysis using a polymer concentration of 0.05 mg ml$^{-1}$
[2]Toxicity determined using MTS assay following 90 min polymer exposure
[3]Median fluorescence of DY647-siRNA in single, focused, live RAW 264.7 cells as determined by ImageStream analysis Analysis of cellular internalization demonstrated rapid and ubiquitous uptake of the DY647-siRNA; over 90% of live cells contained siRNA after only 60 min of exposure. Image analysis of the RAW 264.7 cells and Caco-2 cells indicates a predominately diffuse staining pattern in the cells, suggesting endosomal escape by the siRNA cargo.

From these data, it is clear that inclusion of the MAPA comonomer improves in vitro performance characteristics (lower pH$_c$, greater hemolysis, improved cytocompatibility) relative to the unmodified PDET. Despite decreased performance characteristics relative to PDETB30 (higher pHc, lower hemolysis, comparable cytocompatibility), PDETM30 facilitates efficient intracellular delivery of siRNA.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A composition comprising a hydrogel, the hydrogel comprising a plurality of crosslinked copolymers, wherein each copolymer comprises 2-(diethylamino) ethyl methacrylate (DEAEMA), N-methacryloyl L-phenylalanine methyl ester (MAPA), and poly(ethylene glycol) methyl ether methacrylate (PEGMA).

2. The composition of claim 1, further comprising a plurality of polyoxazoline polymers covalently attached to the hydrogel.

3. The composition of claim 1, further comprising a plurality of polyoxazoline polymers covalently attached to and at least partially disposed on an exterior surface of the hydrogel.

4. The composition of claim 1, further comprising an anionic therapeutic agent or a nucleic acid molecule disposed within the hydrogel.

5. The composition of claim 1, wherein the hydrogel has a positive surface charge at about pH 7.4.

6. The composition of claim 1, wherein the hydrogel has a collapsed structure at about pH 7.4.

7. The composition of claim 1, wherein the hydrogel has a z-average particle size diameter of from about 20 nm to about 200 nm.

8. The composition of claim 1, wherein each copolymer comprises a dimethacrylate crosslinker selected from the group consisting of ethylene glycol dimethacrylate (EGDMA), tetra(ethylene glycol) dimethacrylate (TEGDMA), and poly(ethylene glycol) dimethacrylate (PEGDMA), or combinations thereof.

9. The composition of claim 8, wherein the dimethacrylate crosslinker comprises tetra(ethylene glycol) dimethacrylate (TEGDMA).

10. A method for treating a gastrointestinal disease in a subject comprising: providing at a pH of less than or equal to about 6.5, a pH responsive polycationic hydrogel, the pH responsive polycationic hydrogel comprising a plurality of crosslinked copolymers, wherein each copolymer comprises 2-(diethylamino) ethyl methacrylate (DEAEMA), N-methacryloyl L-phenylalanine methyl ester (MAPA), and poly(ethylene glycol) methyl ether methacrylate (PEGMA), and wherein the pH responsive polycationic hydrogel comprises an anionic therapeutic or a nucleic acid molecule; and introducing the pH responsive polycationic hydrogel to a disease site in the subject's gastrointestinal tract.

11. The method of claim 10, wherein the disease site is selected from the group consisting of a gastrointestinal carcinoma, an active site of Crohn's disease, an active site of ulcerative colitis, and an active site of celiac disease.

* * * * *